United States Patent
Hibner et al.

(10) Patent No.: US 10,575,836 B2
(45) Date of Patent: *Mar. 3, 2020

(54) SURGICAL INSTRUMENT WITH SELECTIVELY LOCKED ARTICULATION ASSEMBLY

(71) Applicant: Ethicon Endo-Surgery, LLC, Guaynabo, PR (US)

(72) Inventors: John A. Hibner, Mason, OH (US); Randal T. Byrum, Mason, OH (US); Karalyn R. Tellio, Cincinnati, OH (US); David C. Groene, Cincinnati, OH (US); Benjamin D. Dickerson, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 235 days.

This patent is subject to a terminal disclaimer.

(21) Appl. No.: 15/089,748

(22) Filed: Apr. 4, 2016

(65) Prior Publication Data
US 2017/0281220 A1    Oct. 5, 2017

(51) Int. Cl.
*A61B 17/00* (2006.01)
*A61B 17/29* (2006.01)
*A61B 17/32* (2006.01)

(52) U.S. Cl.
CPC .... *A61B 17/00234* (2013.01); *A61B 17/2909* (2013.01); *A61B 17/320092* (2013.01);
(Continued)

(58) Field of Classification Search
CPC .......... A61B 17/00234; A61B 17/2909; A61B 17/320092; A61B 2017/00323;
(Continued)

(56) References Cited

U.S. PATENT DOCUMENTS 5,322,055 A    6/1994 Davison et al.
5,873,873 A    2/1999 Smith et al.
(Continued)

FOREIGN PATENT DOCUMENTS

| EP | 0 621 009 A1 | 10/1994 | |
| EP | 2 090 236 A2 | 8/2009 | |
| WO | WO 2012040432 A1 * | 3/2012 | ....... A61B 17/07207 |

OTHER PUBLICATIONS

U.S. Appl. No. 14/258,179, filed Apr. 22, 2014.
(Continued)

*Primary Examiner* — Kathleen S Holwerda
*Assistant Examiner* — Brooke Labranche
(74) *Attorney, Agent, or Firm* — Frost Brown Todd LLC

(57) ABSTRACT

An apparatus for operating on tissue includes a body assembly, a shaft assembly, an acoustic waveguide, an articulation section, an articulation control assembly, an end effector, and an articulation lock. A portion of the articulation section encompasses a flexible portion of the waveguide. The articulation includes a first member and a second member that is longitudinally translatable relative to the first member. The articulation control assembly is configured to move relative to the shaft assembly in order to longitudinally translate the second member relative to the first member. The end effector includes an ultrasonic blade in acoustic communication with the waveguide. The articulation lock is configured to prevent movement of the articulation control assembly relative to the shaft assembly.

20 Claims, 22 Drawing Sheets

(52) U.S. Cl.
CPC .............. *A61B 2017/00327* (2013.01); *A61B 2017/2905* (2013.01); *A61B 2017/2923* (2013.01); *A61B 2017/2925* (2013.01); *A61B 2017/2927* (2013.01); *A61B 2017/2929* (2013.01); *A61B 2017/2946* (2013.01); *A61B 2017/320071* (2017.08); *A61B 2017/320094* (2017.08); *A61B 2017/320095* (2017.08)

(58) Field of Classification Search
CPC ........................................ A61B 2017/00327; A61B 2017/00353; A61B 2017/00734; A61B 2017/2905; A61B 2017/2923; A61B 2017/2925; A61B 2017/2927; A61B 2017/2929; A61B 2017/2946; A61B 18/085; A61B 2018/0225; A61B 18/1445; A61B 2017/003
See application file for complete search history.

(56) References Cited

U.S. PATENT DOCUMENTS

| | | | |
|---|---|---|---|
| 5,897,523 A | 4/1999 | Wright et al. |
| 5,980,510 A | 11/1999 | Tsonton et al. |
| 5,989,264 A | 11/1999 | Wright |
| 6,063,098 A | 5/2000 | Houser et al. |
| 6,090,120 A | 7/2000 | Wright et al. |
| 6,325,811 B1 | 12/2001 | Messerly |
| 6,454,782 B1 | 9/2002 | Schwemberger |
| 6,589,200 B1 | 7/2003 | Schwemberger et al. |
| 6,752,815 B2 | 6/2004 | Beaupre |
| 6,773,444 B2 | 8/2004 | Messerly |
| 6,783,524 B2 | 8/2004 | Anderson et al. |
| 7,135,030 B2 | 11/2006 | Schwemberger et al. |
| 7,621,930 B2 | 11/2009 | Houser |
| 8,461,744 B2 | 6/2013 | Wiener et al. |
| 8,591,536 B2 | 11/2013 | Robertson |
| 8,623,027 B2 | 1/2014 | Price et al. |
| 8,663,220 B2 | 3/2014 | Wiener et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,561,045 B2 | 2/2017 | Hinman et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2010/0193566 A1 | 8/2010 | Scheib et al. |
| 2012/0078247 A1 | 3/2012 | Worrell et al. |
| 2012/0112687 A1 | 5/2012 | Houser et al. |
| 2012/0116265 A1 | 5/2012 | Houser et al. |
| 2013/0289592 A1 | 10/2013 | Stulen et al. |
| 2014/0005701 A1 | 1/2014 | Olson et al. |
| 2014/0005703 A1 | 1/2014 | Stulen et al. |
| 2015/0080924 A1 | 3/2015 | Stulen et al. |
| 2015/0141981 A1 | 5/2015 | Price et al. |
| 2015/0320437 A1 | 11/2015 | Worrell et al. |
| 2015/0351854 A1* | 12/2015 | Hegeman ............. H04B 7/2125 606/1 |

OTHER PUBLICATIONS

U.S. Appl. No. 14/688,458, filed Apr. 16, 2015.
U.S. Appl. No. 14/688,663, filed Apr. 16, 2015.
U.S. Appl. No. 61/410,603, filed Nov. 5, 2010.
International Search Report and Written Opinion dated Sep. 22, 2017 for Application No. PCT/US2017/025952, 19 pgs.

* cited by examiner

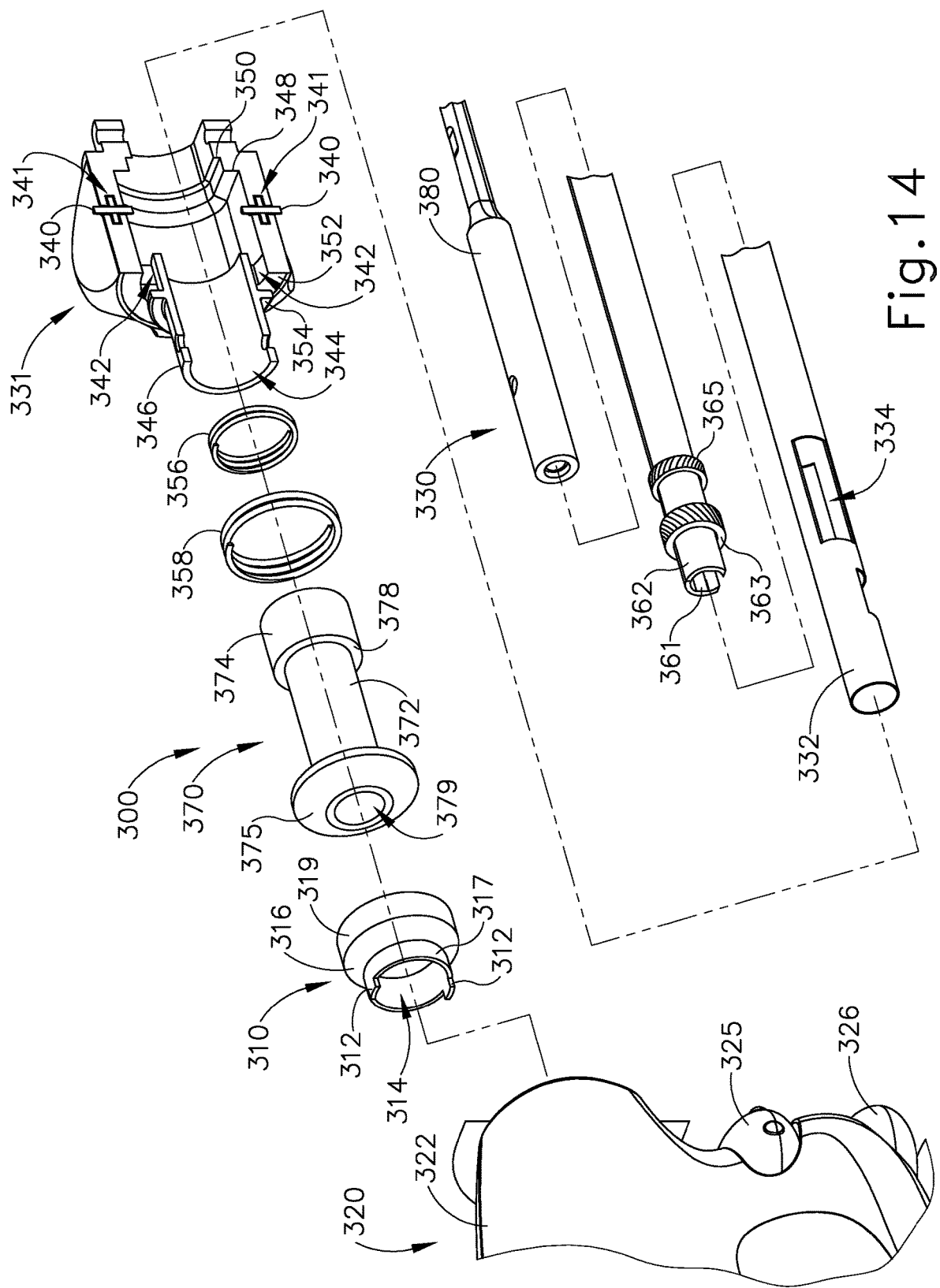

SURGICAL INSTRUMENT WITH SELECTIVELY LOCKED ARTICULATION ASSEMBLY

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No.

2015/0080924, entitled "Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. patent application Ser. No. 14/258,179, entitled "Ultrasonic Surgical Device with Articulating End Effector," filed Apr. 22, 2014, now Provisional App. No. 62/176,880, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 14 depicts an exploded perspective view of the shaft assembly and handle assembly of FIG. 12;

Figure 1:
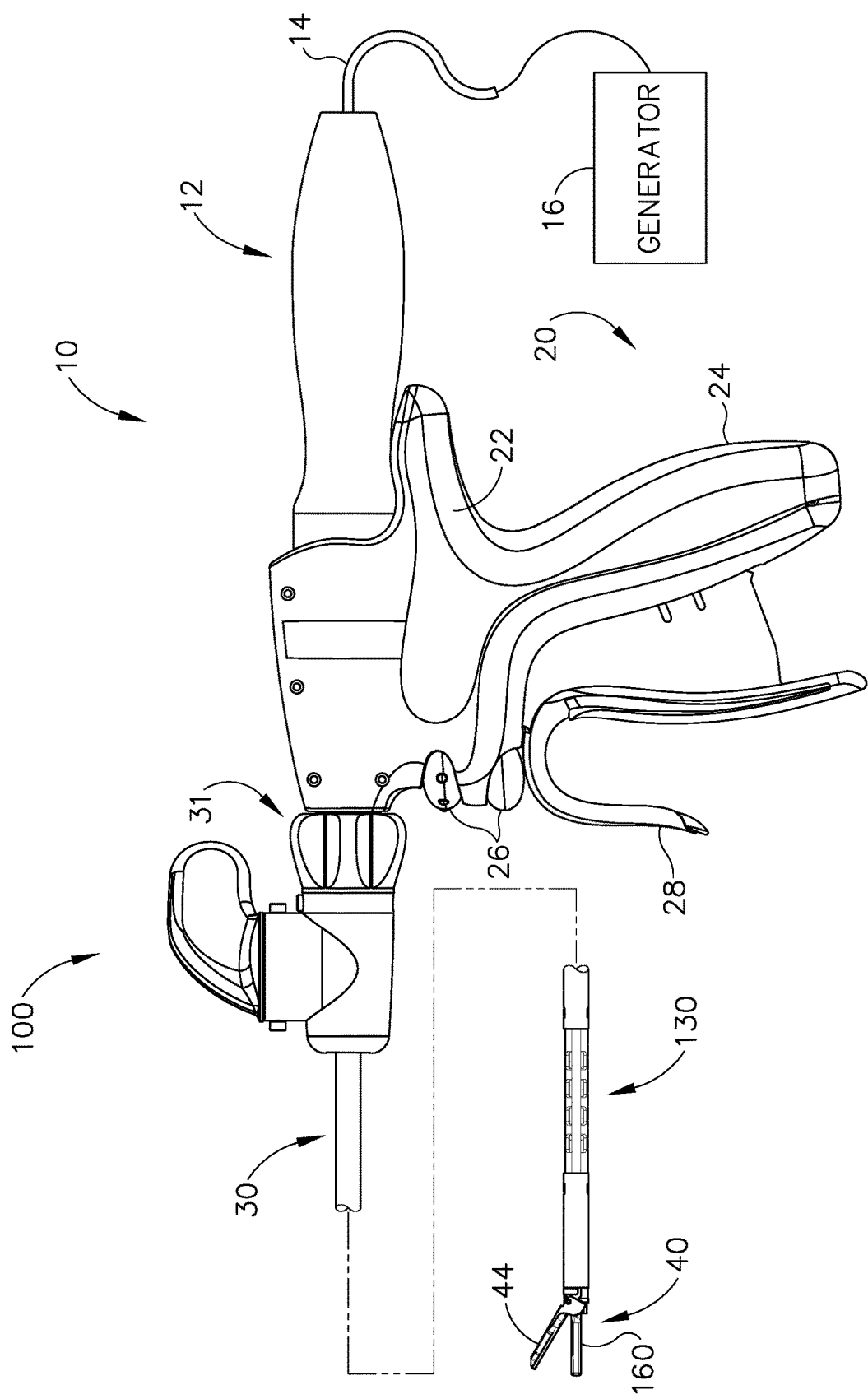
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN04 or GEN11 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
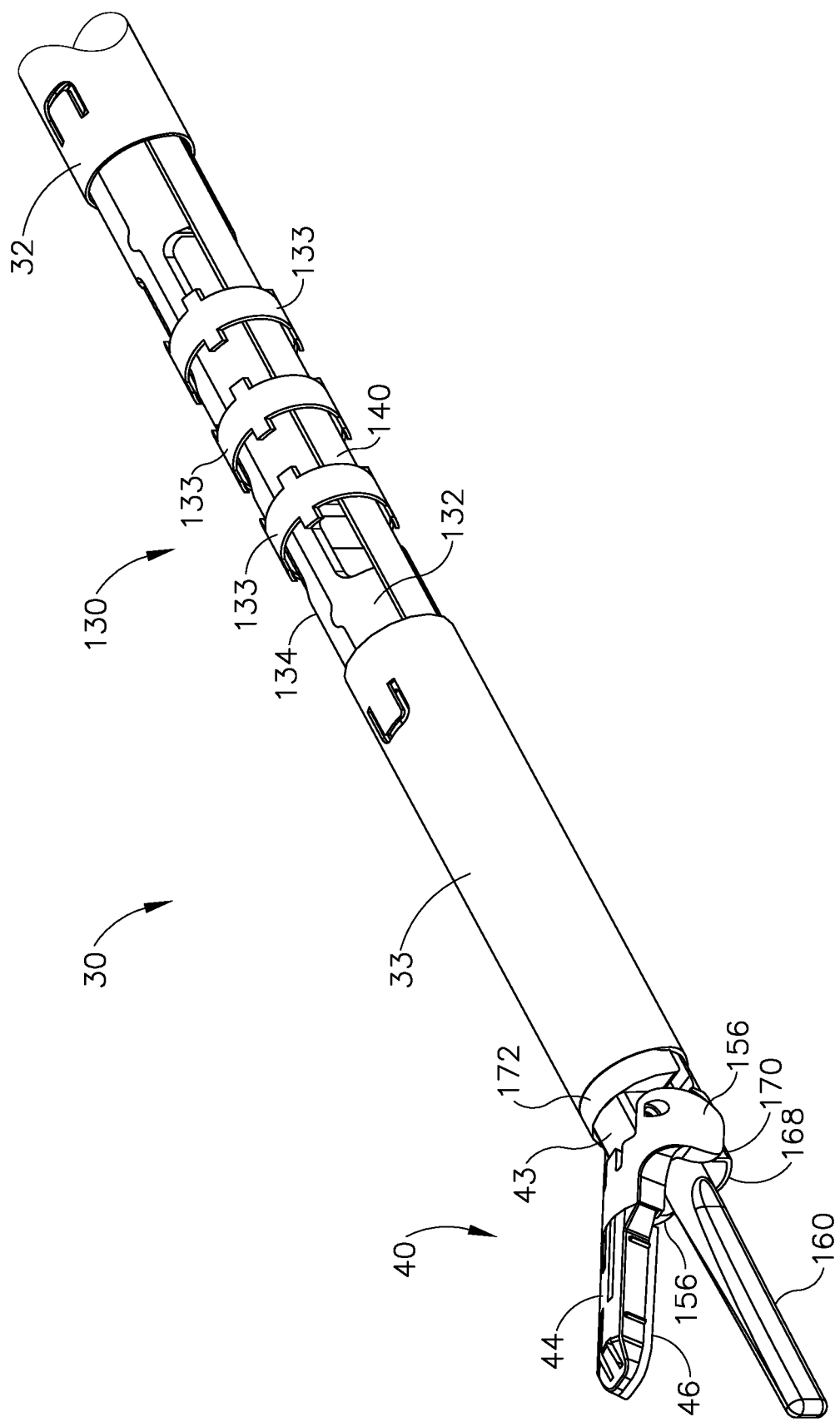
FIG. 2 depicts a perspective view of an articulation section of a shaft assembly and an end effector of the surgical instrument of FIG. 1.
Figure 3:
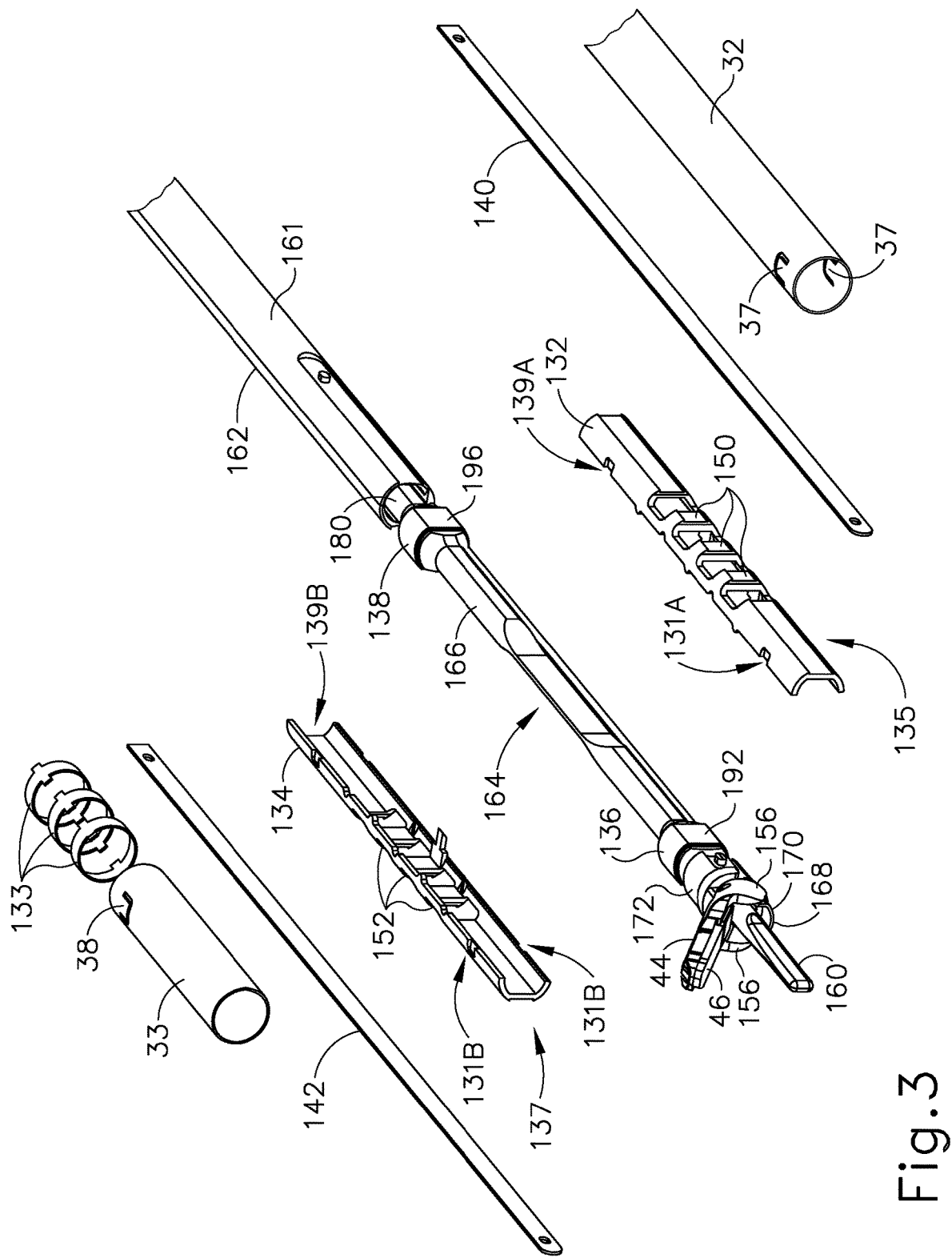
FIG. 3 depicts an exploded perspective view of an articulation section of the shaft assembly of FIG. 2.
Figure 4:
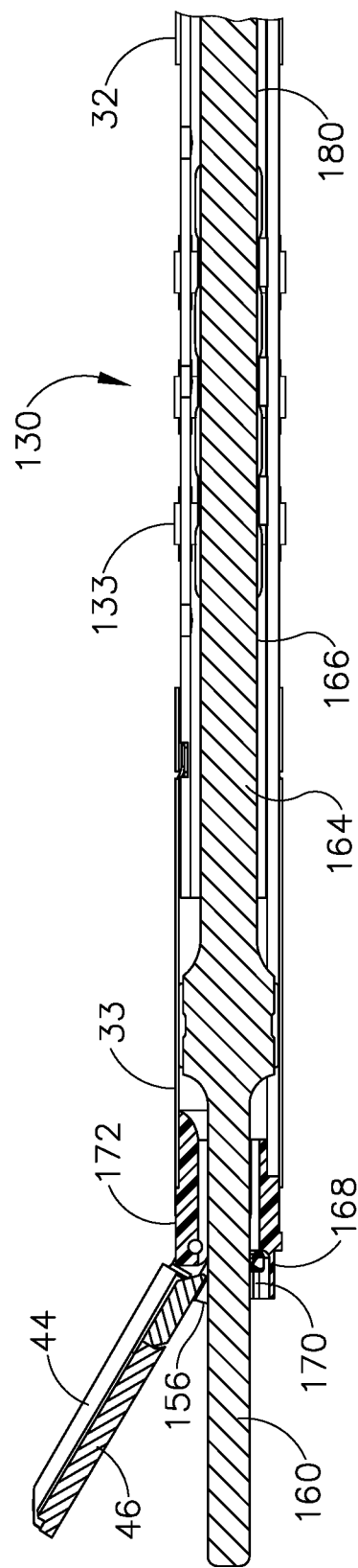
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

In some examples a cable (not shown) may be secured to lower distal shaft element (170). Such a cable may be operable to translate longitudinally relative to an articulation section (130) of shaft assembly (30) to selectively pivot clamp arm (44) toward and away from blade (160). In further examples, the cable is coupled with trigger (28) such that the cable translates proximally in response to pivoting of trigger (28) toward pistol grip (24), and such that clamp arm (44) thereby pivots toward blade (160) in response to pivoting of trigger (28) toward pistol grip (24). In addition, the cable may translate distally in response to pivoting of trigger (28) away from pistol grip (24), such that clamp arm (44) pivots away from blade (160) in response to pivoting of trigger (28) away from pistol grip (24). Alternatively, the cable may be secured to proximal outer sheath (32). Proximal outer sheath (32) may be coupled with trigger (28) such that the cable and outer sheath (32) translates proximally in response to pivoting of trigger (28) toward pistol grip (24); and such that clamp arm (44) thereby pivots toward blade (160) in response to pivoting of trigger (28) toward pistol grip (24). In addition, the cable and outer sheath (32) may translate distally in response to pivoting of trigger (28) away from pistol grip (24), such that clamp arm (44) pivots away from blade (160) in response to pivoting of trigger (28) away from pistol grip (24). Clamp arm (44) may be biased toward the open position, such that (at least in some instances) the operator may effectively open clamp arm (44) by releasing a grip on trigger (28).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). Transducer assembly (12) includes a set of piezoelectric discs (not shown) located proximal to a horn (not shown) of waveguide (180). The piezoelectric discs are operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180) (i.e. locations where the vibrational amplitude is minimal). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

Those of ordinary skill in the art will understand that, as a matter of physics, the distal end of blade (160) is located at a position corresponding to an anti-node associated with resonant ultrasonic vibrations communicated through flexible portion (166) of waveguide (180). When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread.

In some versions, end effector (40) is operable to apply radiofrequency (RF) electrosurgical energy to tissue in addition to applying ultrasonic energy to tissue. By way of example only, end effector (40) may be configured and operable in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and/or U.S. Pat. No. 8,663,220, entitled "Ultrasonic Electrosurgical Instruments," issued Mar. 4, 2014, the disclosure of which is incorporated by reference herein.

Other suitable configurations for an acoustic transmission assembly and transducer assembly (12) will be apparent to one or ordinary skill in the art in view of the fteachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-6C, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a knob (31) is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (130) may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. Various other suitable forms that articulation section (130) may take will be apparent to those of ordinary skill in the art in view of the teachings herein.

As best seen in FIGS. 2-6CB articulation section (130) of this example comprises a set of three outer rings (133) and a pair of ribbed body portions (132, 134), with a pair of articulation bands (140, 142) extending along respective channels (135, 137) defined between interior surfaces of outer rings (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

Figure 5:
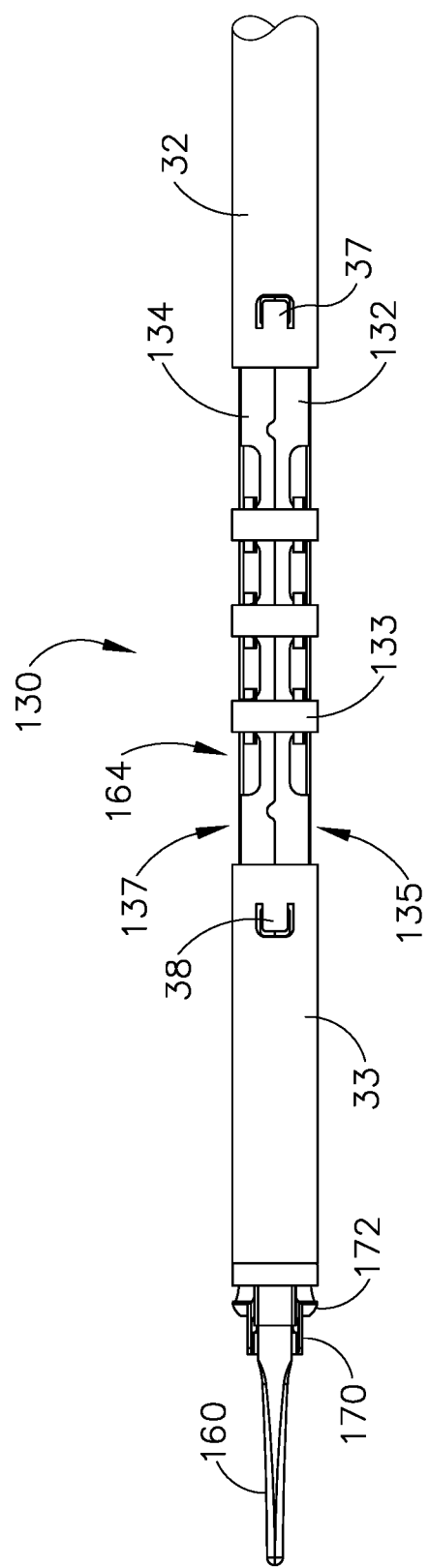
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
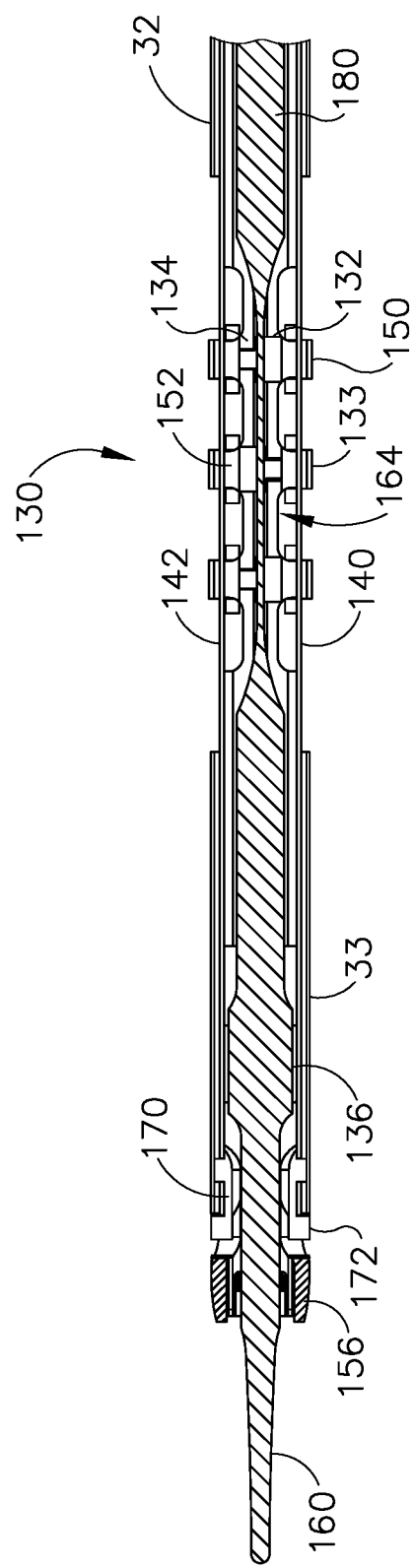
FIG. 6A depicts a cross-sectional top view of the shaft assembly and end effector of FIG. 2 in a straight configuration.
Figure 6B:
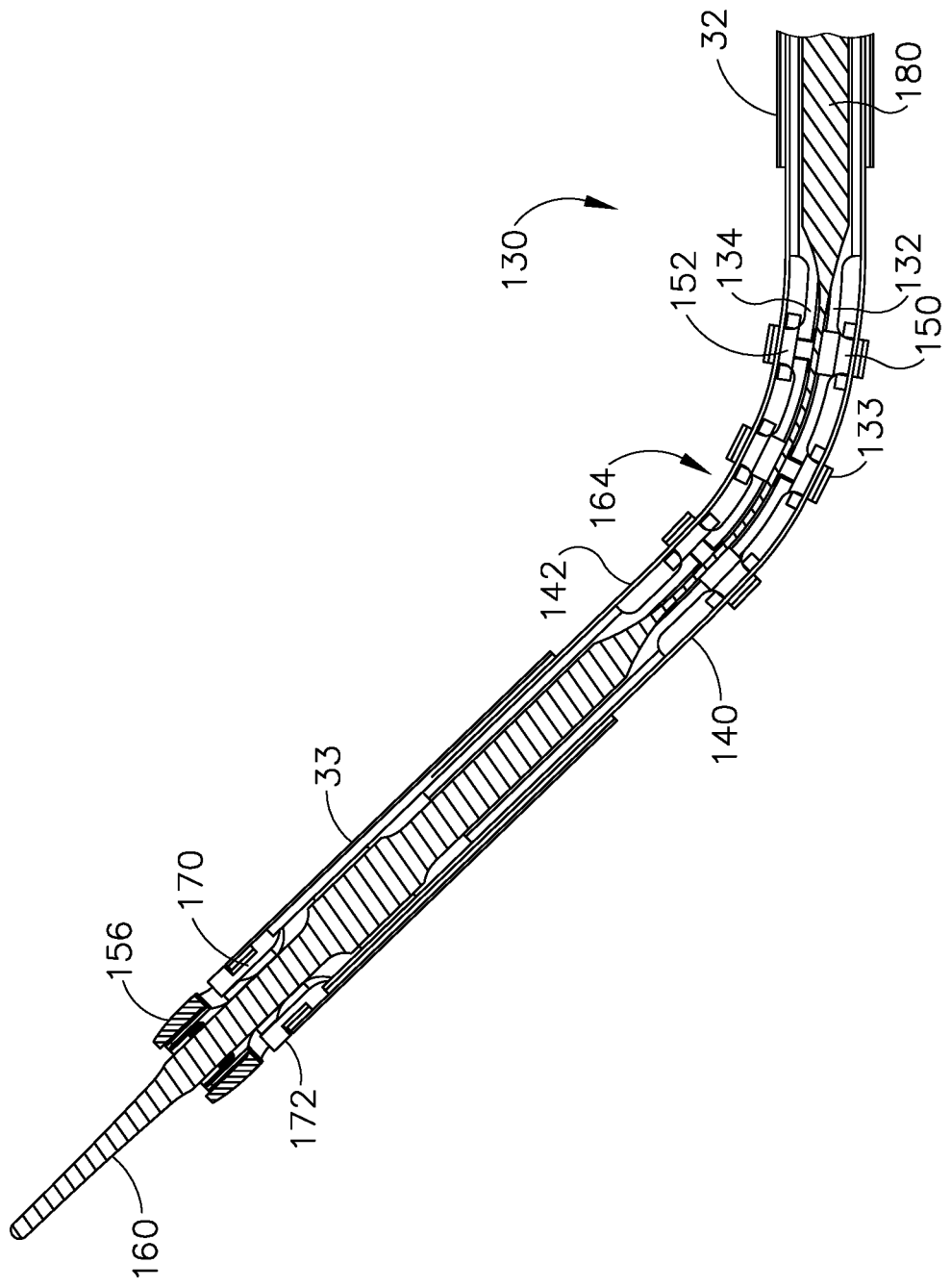
FIG. 6B depicts a cross-sectional top view of the shaft assembly and end effector of FIG. 2 in a first articulated configuration.
Figure 6C:
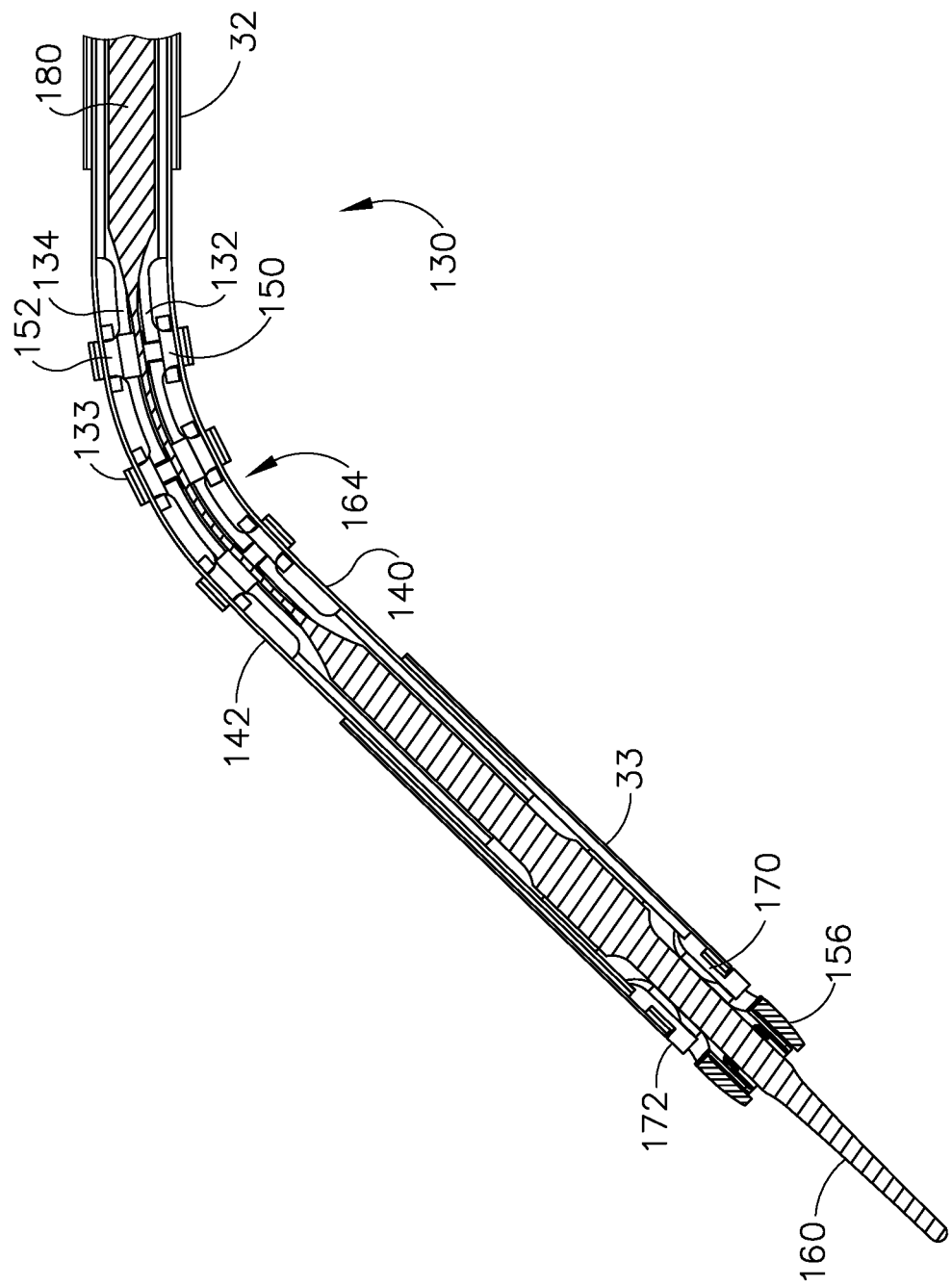
FIG. 6C depicts a cross-sectional top view of the shaft assembly and end effector of FIG. 2 in a second articulated configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to an first articulated configuration as shown in FIG. 6B or a second articulated configuration as shown in FIG. 6C. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIGS. 6B-6C.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32); while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. Pub. No. 2013/0289592, entitled "Ultrasonic Device for Cutting and Coagulating," published Oct. 31, 2013, issued as U.S. Pat. No. 10,238,416 on Mar. 26, 2019, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIGS. 6B-6C). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

Figure 7:
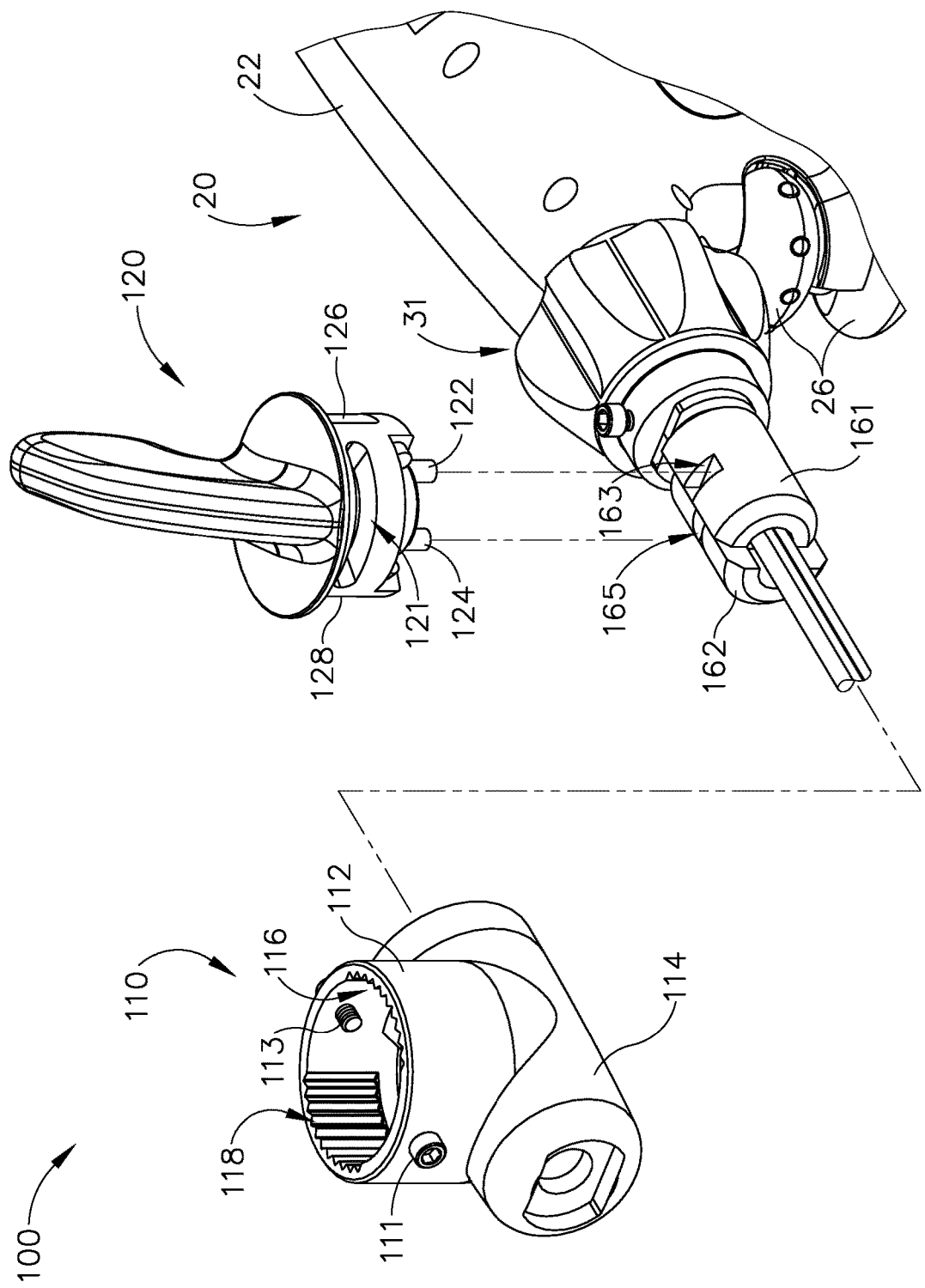
FIG. 7 depicts a partially exploded perspective view of an articulation control assembly of the instrument of FIG. 1.
Figure 8:
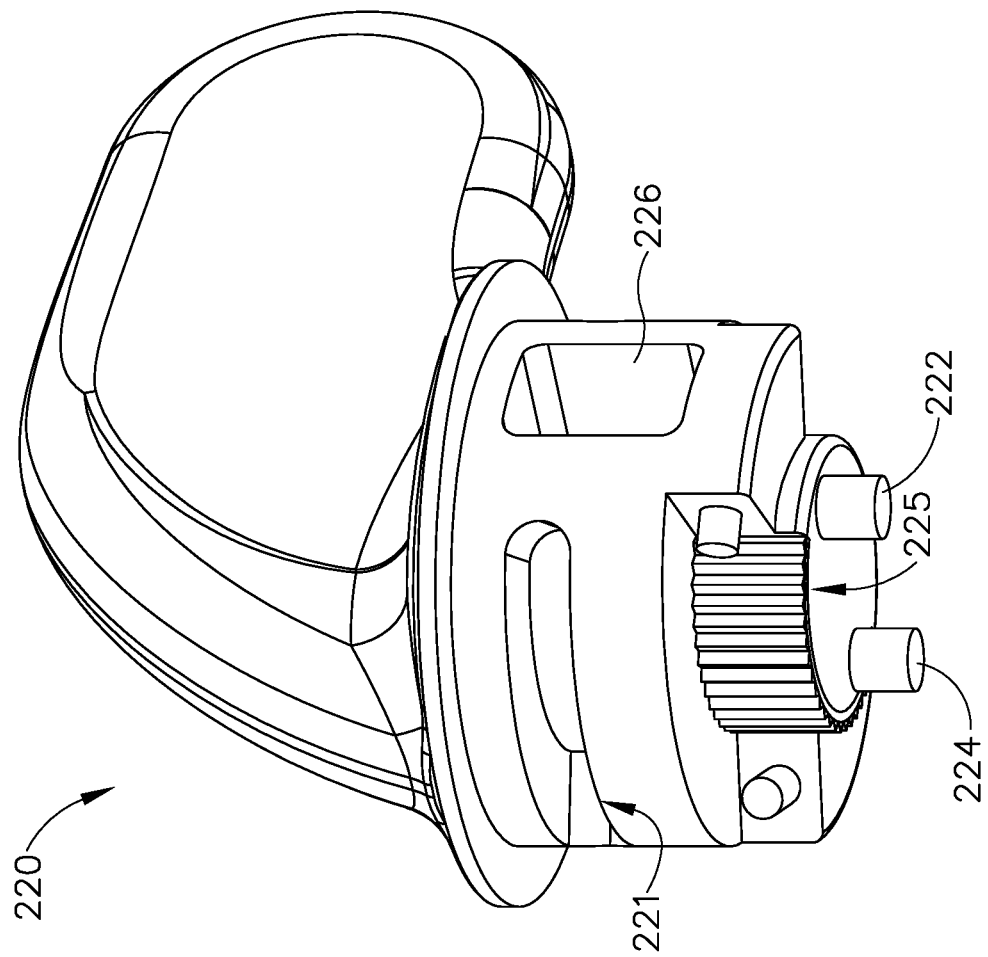
FIG. 8 depicts a perspective view of an alternative rotatable knob that may be readily incorporated into the surgical instrument of FIG. 1.
Figure 9:
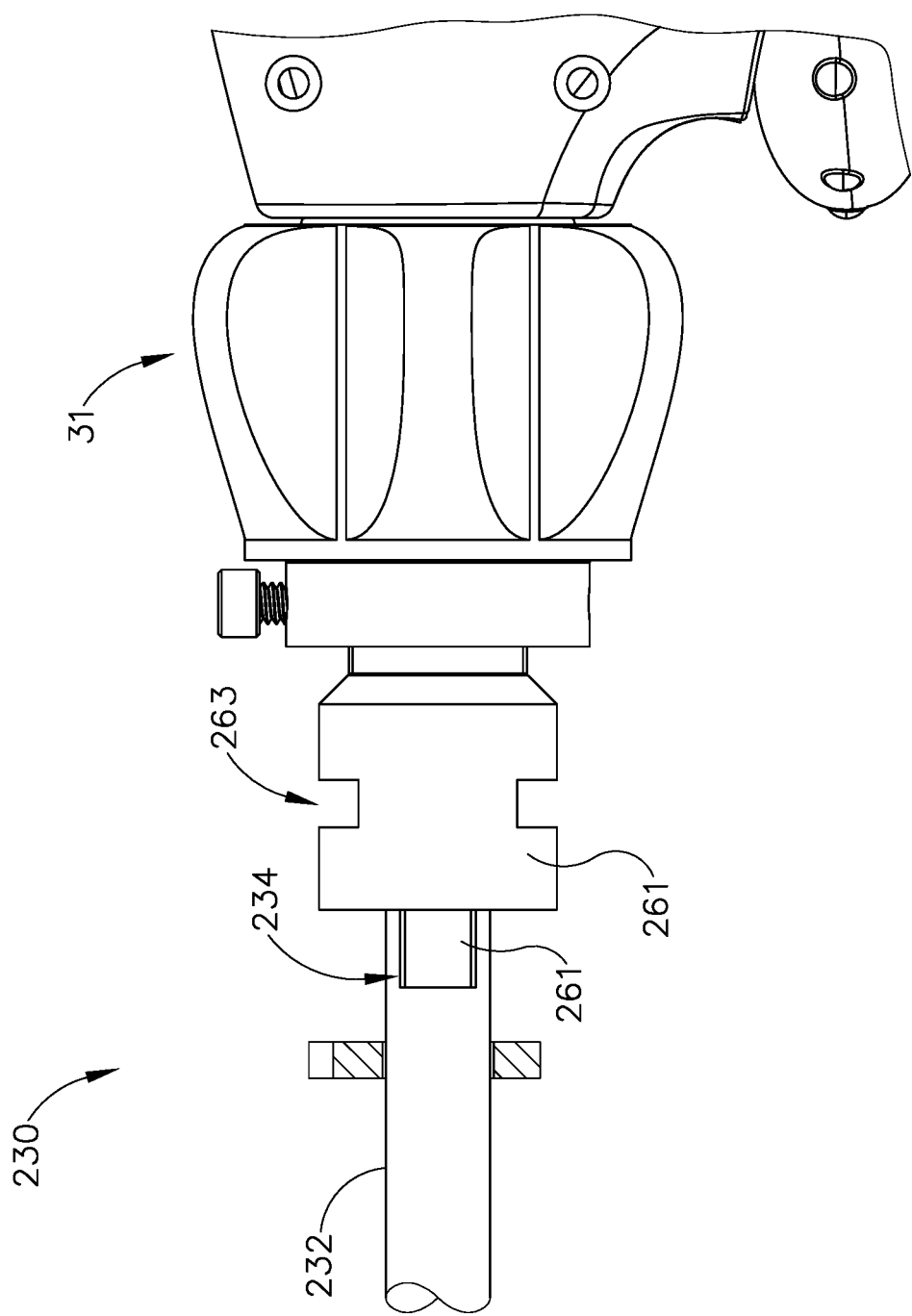
FIG. 9 depicts a side elevational view of an alternative shaft assembly that may be readily incorporated into the surgical instrument of FIG. 1.

As best seen in FIG. 7, an articulation control assembly (100) is secured to a proximal portion of outer sheath (32). Articulation control assembly (100) comprises a housing (110) and a rotatable knob (120). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163, 165) formed in top surfaces of translatable members (161, 162). Channels (163, 165) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In addition to or in lieu of the foregoing, articulation section (130) and/or articulation control assembly (100) may be constructed and/or operable in accordance with at least some of the teachings of U.S. patent application Ser. No. 14/688,458, entitled "Ultrasonic Surgical Instrument with Rigidizing Articulation Drive Members," filed on Apr. 16, 2015, issued as U.S. Pat. No. 10,034,683 on Jul. 31, 2018. Alternatively, articulation section (130) and/or articulation control assembly (100) may be constructed and/or operable in any other suitable fashion.

II. Exemplary Articulation Section Locking Features

In some instances, it may be desirable to selectively lock articulation section (130) in various articulation angles. In other words, it may be desirable to selectively prevent further deflection of end effector (40) relative to the longitudinal axis defined by proximal outer sheath (32). Locking articulation section (130) may prevent a user from inadvertently articulating (or de-articulating) end effector (40) during use of instrument (10) in a surgical procedure. In some instances, it may also be desirable to simultaneously or independently lock rotatable features, such as knob (31) described above. A user may thus be prevented from inadvertently rotating shaft assembly (30) about the longitudinal axis defined by outer sheath (32) during use of instrument (10) in a surgical procedure.

A. Locking Features Associated with Trigger Closure

FIGS. 8-11B show an alternative rotatable knob (220), alternative shaft assembly (230), and alternative trigger (228) that may be readily incorporated into instrument (10). Knob (220) is substantially similar to knob (120), with the differences described below. Knob (220) includes an arcuate channel (221), engagement member (226), pins (222, 224), and set screws (211, 213); which are substantially similar to arcuate channel (121), engagement member (126), pins (122, 124), and set screws (111, 113), respectively, described above. Also similar to knob (120), knob (220) is rotatably disposed within a first hollow cylindrical portion (112) of housing (110) such that knob (220) is operable to rotate within cylindrical portion (112) of housing (110). Pins (222, 224) extend into second cylindrical portion (114) of housing (110) and are rotatably and slidably disposed within a respective pair of channels (263, 265) formed in top surfaces of translatable members (261, 262). Channels (263, 265) are positioned on opposite sides of an axis of rotation of knob (220), such that rotation of knob (220) about that axis causes opposing longitudinal translation of translatable members (261, 262).

Unlike knob (120) described above, knob (220) of the present example also includes an annular array of distally presented teeth (225). As will be described in greater detail below, teeth (225) of knob (220) may selectively lock with portions of shaft assembly (230) in order to help lock articulation of end effector (40).

Shaft assembly (230) is substantially similar to shaft assembly (30) described above, with differences described below. Shaft assembly (230) includes a proximal outer shaft (232), translatable members (261, 262), a pair of channels (263, 265), and a waveguide (280); all of which are substantially similar to proximal outer shaft (32), translatable members (161, 162), channels (163, 165), and waveguide (180), respectively, as described above. It should be understood that translatable members (261, 262) and waveguide (280) will be attached to articulation section (130) and end effector (40) in substantially the same manner as translatable members (161, 162) and waveguide (180) described above. Therefore, translatable members (261, 262) may be mechanically coupled with articulation bands (140, 142) while waveguide (280) may transition into narrowed section (164) and ultrasonic blade (160); similar to that seen in FIG. 3. Also similar to shaft assembly (30), a proximal portion of outer sheath (232) may be connected to knob (31) such that shaft assembly (230) is rotatable about the longitudinal axis defined by outer sheath (232), relative to handle assembly (20). Of course, rotatable features may simply be omitted if desired.

Figure 10A:
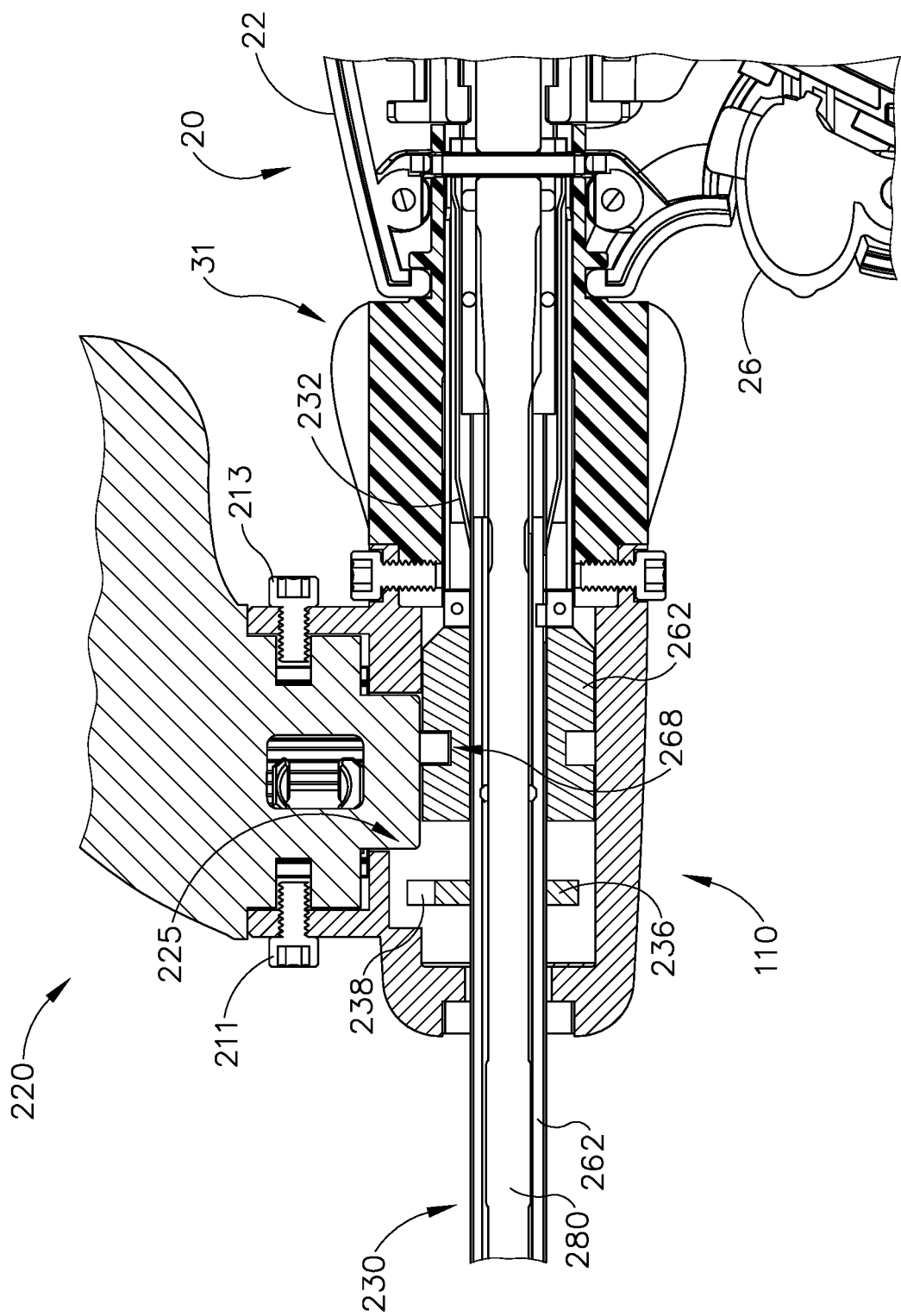
FIG. 10A depicts a side cross-sectional view of the rotatable knob of FIG. 8 and the shaft assembly of FIG. 9 incorporated into the surgical instrument of FIG. 1, where the instrument is in a non-clamping configuration.
Figure 10B:
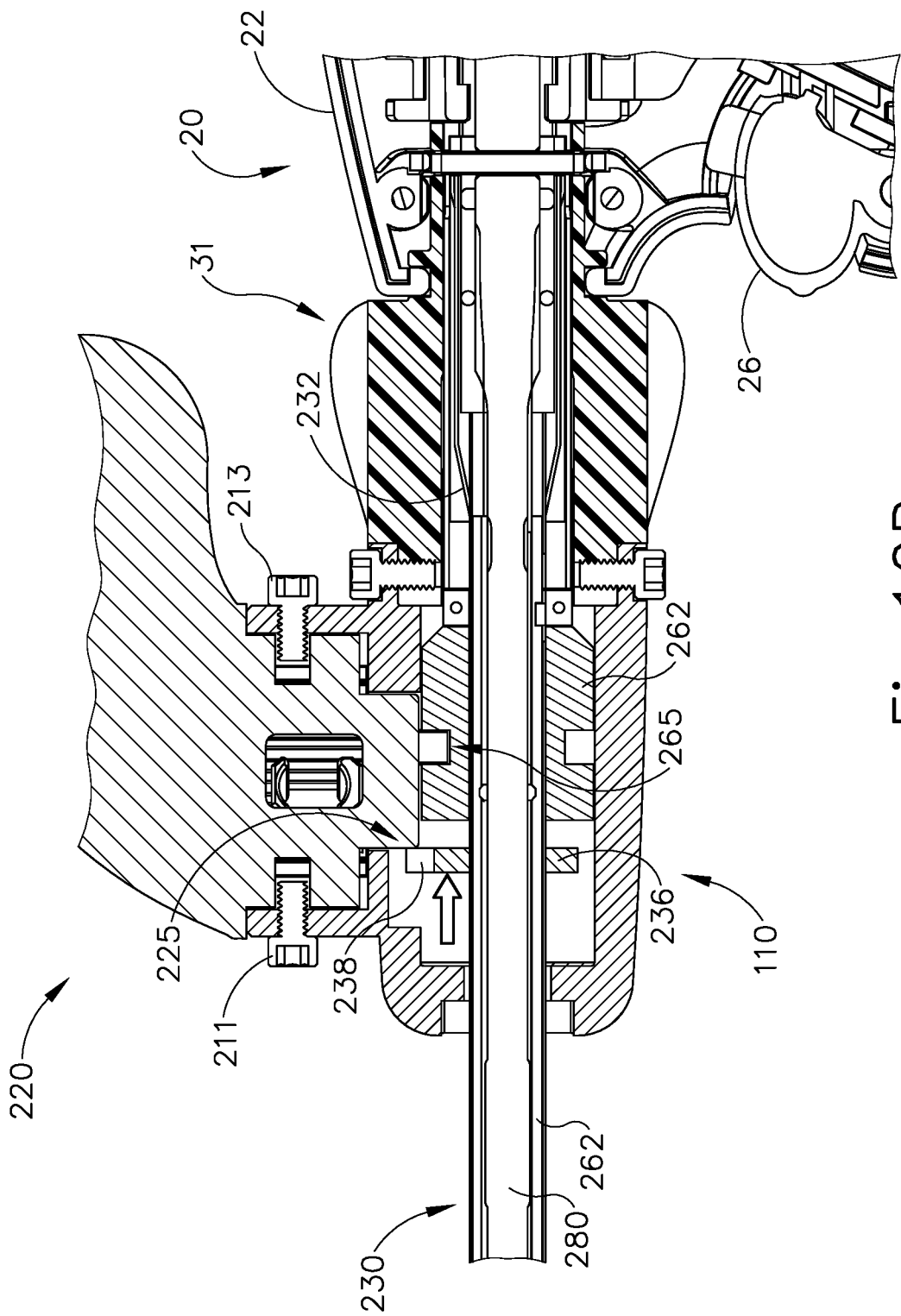
FIG. 10B depicts a side cross-sectional view of the rotatable knob of FIG. 8 and the shaft assembly of FIG. 9 incorporated into the surgical instrument of FIG. 1, where the instrument is in a clamping configuration.

Shaft assembly (230) includes a radial mounting ring (236) with an annular array of pins (238) projecting from the exterior of mounting ring (236). Mounting ring (236) is fixed to proximal outer shaft (232). As previously described above for proximal outer shaft (32) and trigger (28), proximal outer shaft (232) is coupled with trigger (228) such that outer sheath (232) translates proximally in response to pivoting of trigger (228) toward pistol grip (24). As shown in FIGS. 10A-10B, pins (328) project from the exterior of mounting ring (236) in such a manner that the top pin (238) will mesh with distal facing teeth (225) when trigger (228) is pivoted toward pistol grip (24).

Figure 11A:
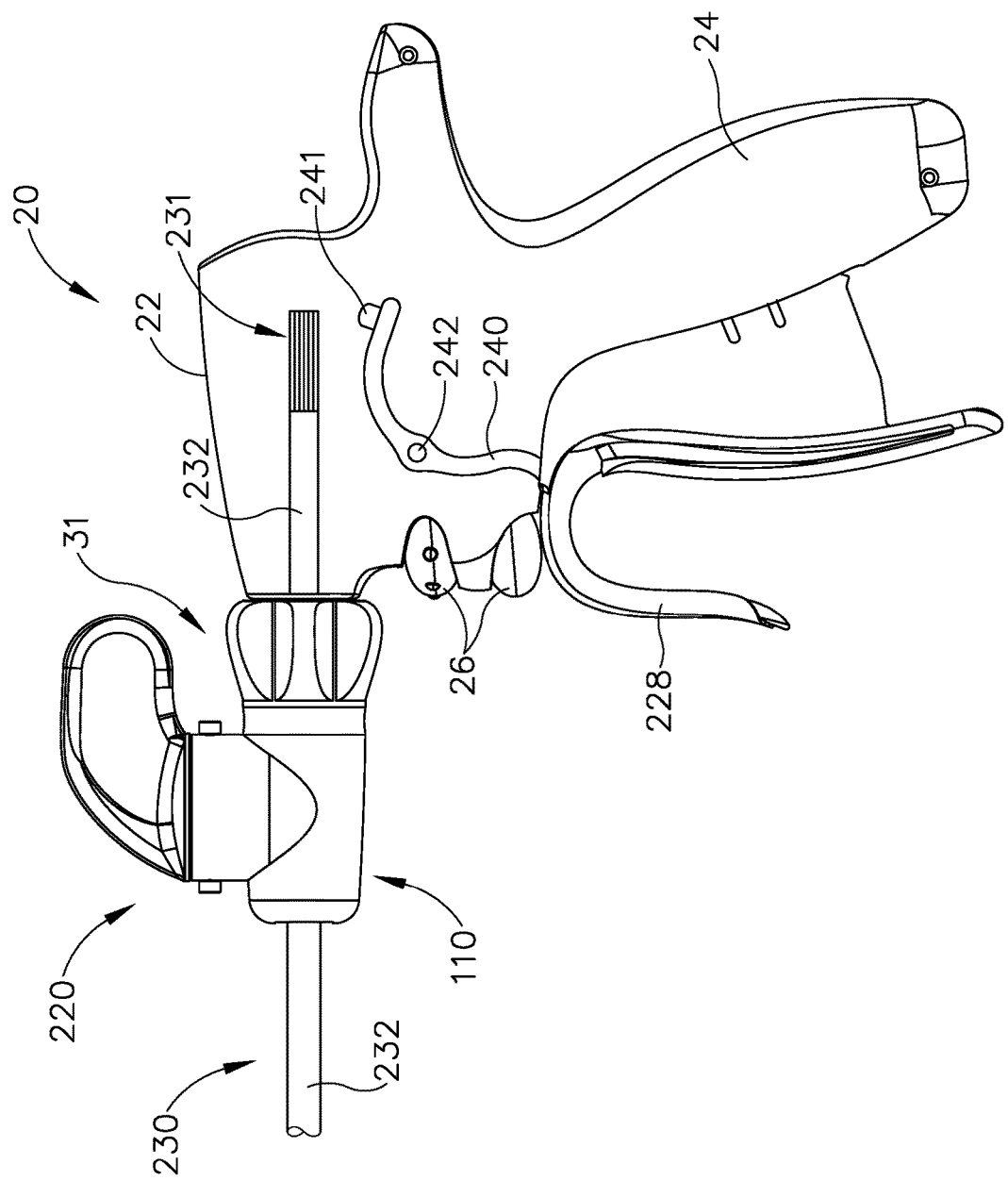
FIG. 11A depicts a side elevational view of the rotatable knob of FIG. 8 and the shaft assembly of FIG. 9 incorporated into the surgical instrument of FIG. 1, with half the body omitted for clarity, where the instrument is in an non-clamping configuration.
Figure 11B:
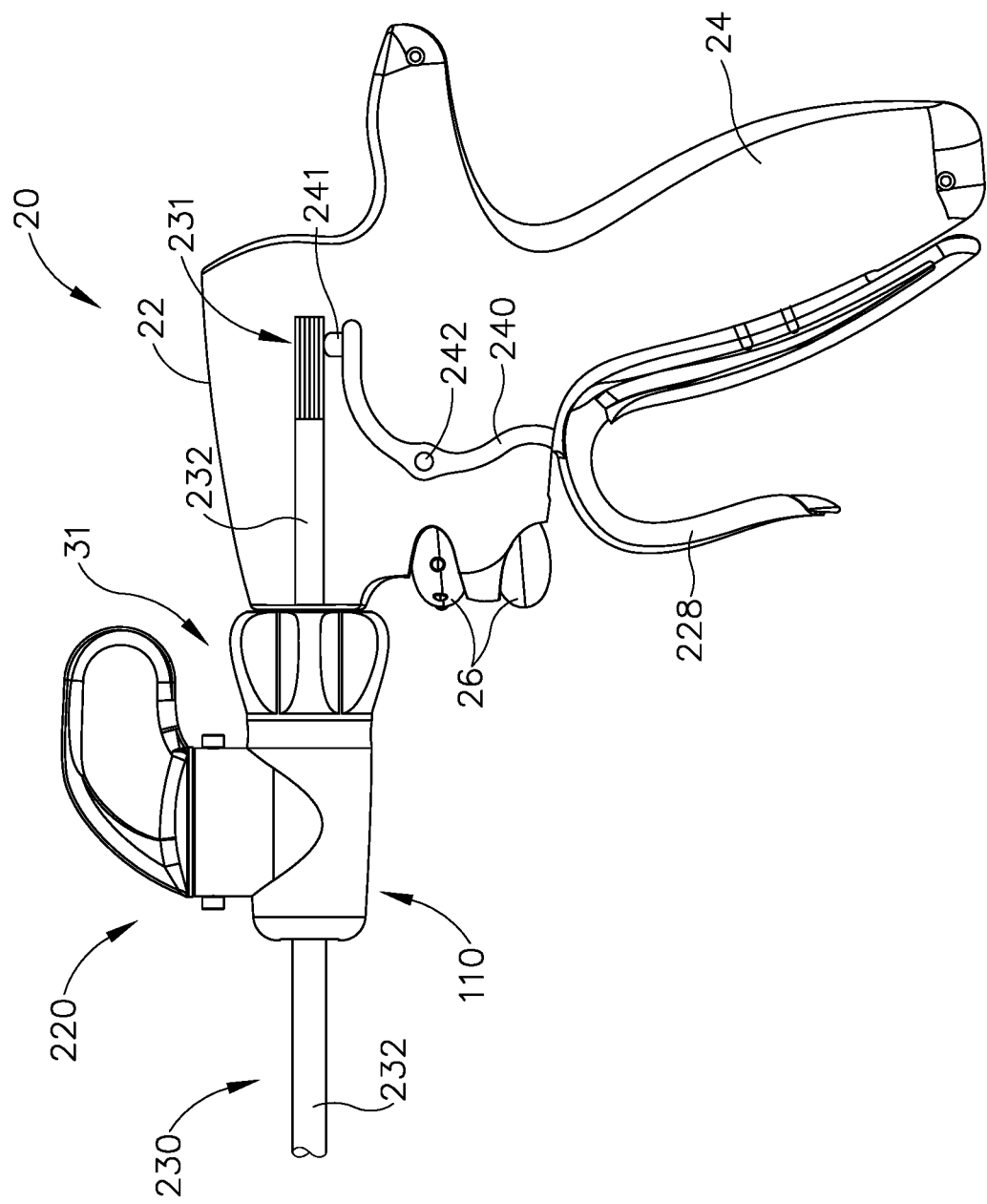
FIG. 11B depicts a side elevational view of the rotatable knob of FIG. 8 and the shaft assembly of FIG. 9 incorporated into the surgical instrument of FIG. 1, with half the body omitted for clarity, where the instrument is in a clamping configuration.
Figure 12:
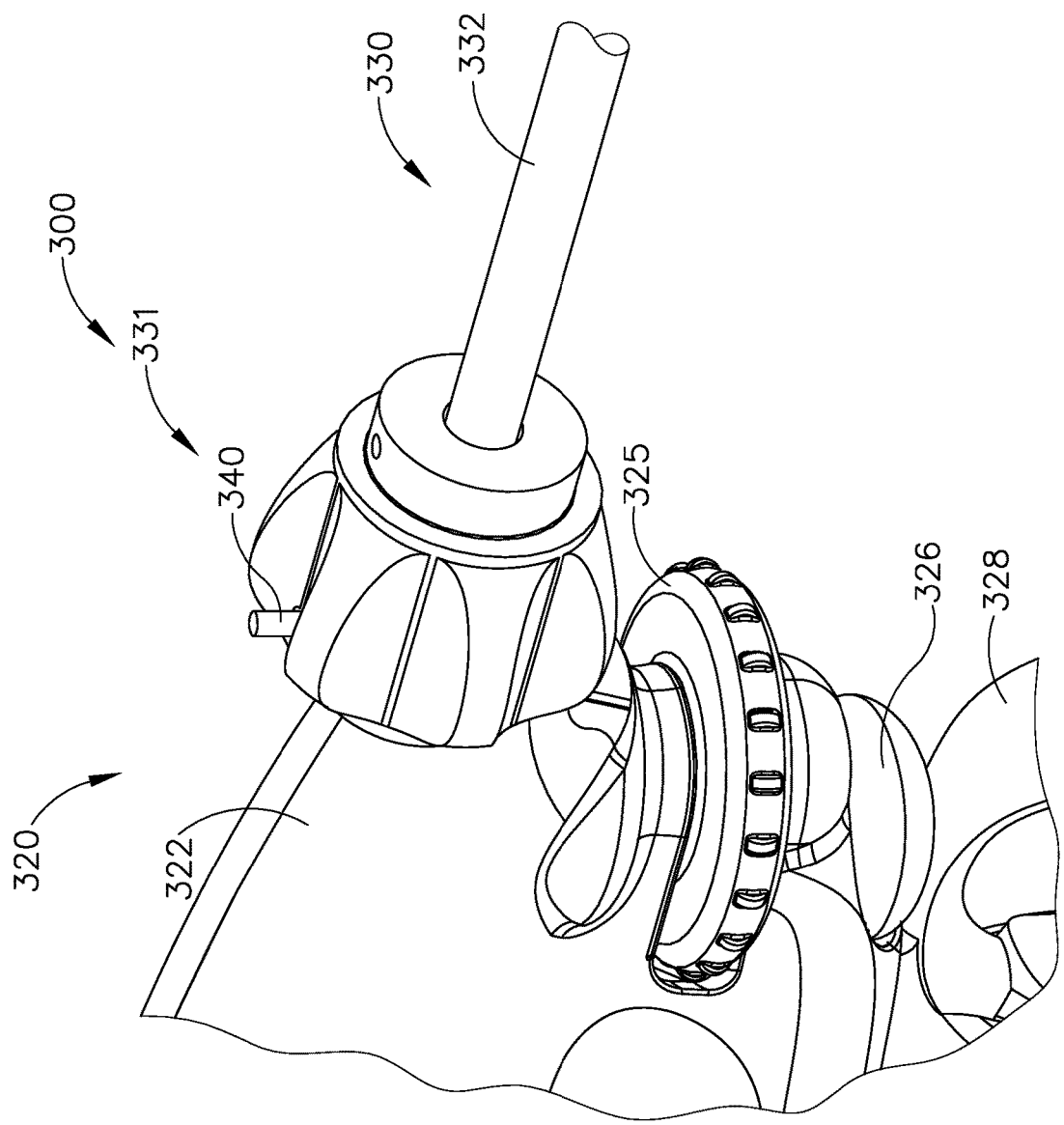
FIG. 12 depicts a perspective view of an alternative handle assembly and another alternative shaft assembly that may be readily incorporated into the instrument of FIG. 1.
Figure 13:
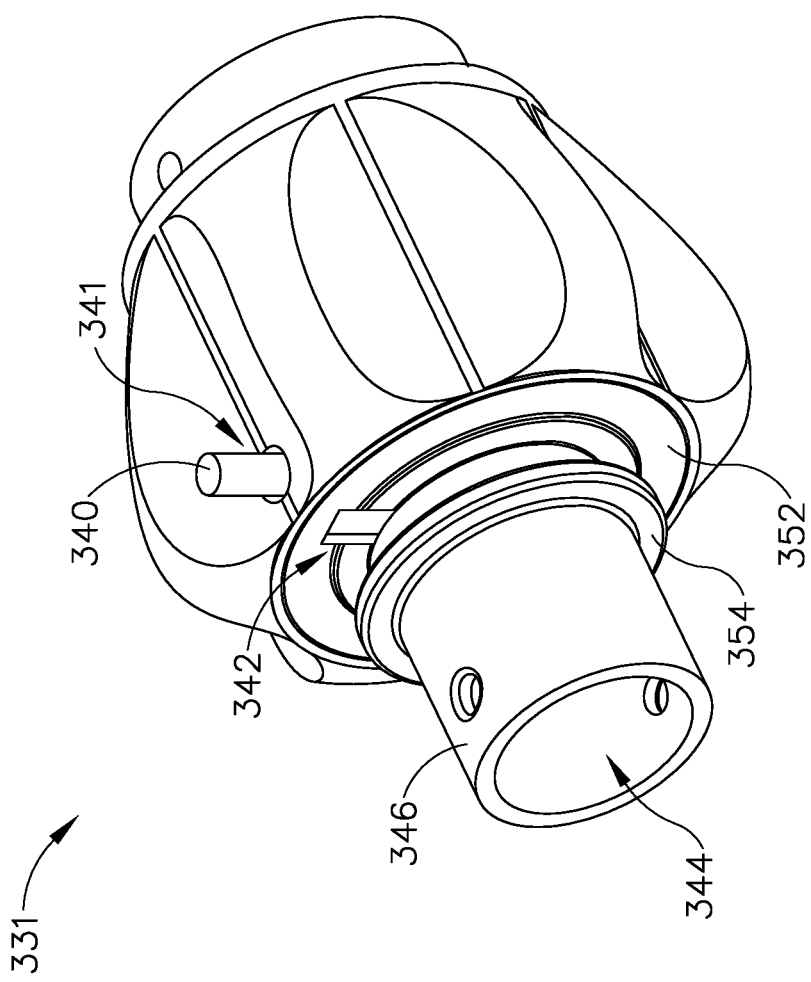
FIG. 13 depicts a perspective view of the alternative knob of the shaft assembly of FIG. 12.

Additionally, as seen in FIGS. 11A-11B, trigger (228) includes a lever (240), a pin (241), and a pivot (242). Lever (240) is pivotally fixed to handle assembly (22) via pivot (242). Pin (241) is attached to the end of lever (240) opposite of trigger (28). As shown in FIGS. 11A-11B, as trigger (228) is pivoted toward pistol grip (24), lever (240) rotates about pivot (242) until trigger (228) completes a range of pivotal motion. When trigger (228) is fully closed against pistol grip (24), pin (241) is configured to mesh against splines (231) of proximal outer sheath (232). In some other versions, pin (241) may reach a position where pin (241) meshes with splines (231) before trigger (228) actually reaches pistol grip (24).

It should be understood from the foregoing that, when trigger (228) completes a full range of pivotal motion, top pin (238) meshes against distal facing teeth (225) while pin (242) simultaneously meshes against splines (2310) of proximal outer sheath (232). With pin (241) meshing against splines (231), the rotational position of shaft assembly (230) about the longitudinal axis defined by proximal outer shaft (232) is locked. Additionally, with top pin (238) meshing against distal facing teeth (225), rotation knob (220) is rotationally fixed relative to first hollow cylindrical portion (112). Thus, pins (222, 224) are rotationally fixed, such that translatable members (261, 262) are longitudinally fixed. With translatable members (261, 262) being mechanically coupled to articulations bands (140, 142), articulation bands (140, 142) are also longitudinally fixed. Therefore, the articulated position of end effector (40) is fixed (regardless of whether articulation section (130) is in a straight configuration or a bent configuration). In other words, when trigger (228) completes a full range of pivotal motion, the rotational position of proximal outer sheath (232) and the articulated position (40) of end effector (40) are both locked. This prevents end effector (40) from inadvertently rotating about the longitudinal axis or deflecting laterally relative to the longitudinal axis when clamp arm (44) is in a closed position. This will further prevent inadvertent damage to tissue clamped between clamp arm (44) and blade (160) that might otherwise occur if end effector (40) is inadvertently rotated about the longitudinal axis or deflected laterally relative to the longitudinal axis.

B. Locking Features with Biased Engagement

FIGS. 12-15D show an articulation control assembly (300), a conical lock (310), a knob (331), a handle assembly (320), and a shaft assembly (330) that may be readily incorporated into instrument (10) described above. Handle assembly (320) is substantially similar to handle assembly (20) described above, with the differences described below. In particular, handle assembly (320) includes a body (322) and a button (326) that are substantially similar to body (22) and button (26) described above. However, handle assembly (320) also includes an articulation finger wheel (325). As will be described in greater detail below, articulation finger wheel (325) is capable of selectively controlling articulation control assembly (300) to articulate end effector (40) relative to a longitudinal axis (L2) defined by a proximal outer sheath (332) of shaft assembly (330). By way of example only, finger wheel (325) may be operable to drive articulation of end effector (40) in accordance with at least some of the teachings of U.S. patent application Ser. No. 14/688,663, entitled "Ultrasonic Surgical Instrument with Opposing Thread Drive for End Effector Articulation," filed Apr. 16, 2015, issued as U.S. Pat. No. 10,342,567 on Jul. 9, 2019, the disclosure of which is incorporated by reference herein.

Shaft assembly (330) includes a waveguide (380), a pair of translating members (361, 362), and a proximal outer shaft (332). Waveguide (380) is substantially similar to waveguide (180, 280) mentioned above. A proximal end of waveguide (380) extends through knob (331), articulation drive shaft (370), and conical lock (310) into handle assembly (320). Translating member (361) is substantially similar to translating member (161, 261) mentioned above, with differences described below. Additionally, translating member (362) is substantially similar to translating member (162, 262) described above, with differences described below. Therefore, translatable members (361, 362) may be mechanically coupled with articulation bands (140, 142) while waveguide (280) may transition into narrowed section (164) and ultrasonic blade (160); similar to that seen in FIG. 3. However, instead of defining channels (163, 165, 263, 265), translatable members (361, 362) are fixed to a respective translating gear drive (363, 365). As will be described in greater detail below, translating gear drives (363, 365) are configured as lead screws with threading that mesh with a selected portion of articulation control assembly (300) in order to translate translating members (361, 362) to articulate end effector (40) relative to longitudinal axis (L2) defined by proximal outer sheath (332) of shaft assembly (330).

Waveguide (380) is housed within translating members (361, 362), while translating members (361, 362) are housed within proximal outer shaft (332). Proximal outer shaft (332) defines slots (334) for translating drive gears (363, 365) to protrude from in order to mate with articulation drive shaft (370), as will be described below.

Knob (331) is substantially similar to knob (31, 231) described above in that a proximal portion of outer sheath (332) may be connected to knob (331) such that knob (331) may rotate shaft assembly (330) about longitudinal axis (L2) defined by outer sheath (332). Knob (331) includes a proximal sleeve (346), a radial protrusion (354), a proximal exterior surface (352), a first annular wall (348), a second annular wall (350), a pair of biasing springs (356, 358), and a pair of unlocking pins (340) slidably housed within respective pin slots (341). Knob (331) defines a cavity (344) that partially houses articulation drive shaft (370) and conical rotation lock (310). Knob (331) also defines a pair of locking slots (342) extending from proximal exterior wall (342) into cavity (344). Biasing spring (358) is housed within first annular wall (348) of knob (331) while biasing spring (356) is housed within second annular wall (350) of knob (331) As will be described in greater detail below, unlocking pins (340) may be pressed inwardly to enable unitary rotation of knob (331) and shaft assembly (330) about longitudinal axis (L2) defined by proximal outer shaft (332); and to enable translation of translating members (361, 362) to articulate end effector (40) relative to longitudinal axis (L2).

Articulation control assembly (300) includes an articulation drive shaft (370), a drive shaft (315) unitarily connected to articulation finger wheel (325), and a bevel gear (335) unitarily fixed to the other end of drive shaft (315). Articulation finger wheel (325) is rotatably fixed to body (322) via pin (311). Pin (311) defines axis (L1), which articulation finger wheel (325), drive shaft (315) and bevel gear (335) rotate about. Articulation drive shaft (370) includes a hollow shaft (372), a bevel gear (375), and a rotating drive gear (374). Articulation drive shaft (370) also defines a hollow portion (379) that partially houses proximal outer shaft (332), waveguide (380), and translating members (361, 362). Bevel gear (375) is fixed to a proximal end of hollow shaft (372) while rotating drive gear (374) is fixed to a distal end of hollow shaft (372). Bevel gears (335, 375) are configured to mesh with each other such that rotation of bevel gear (335) about axis (L1) causes rotation of bevel gear (375) about axis (L2). Because bevel gear (375) is unitarily fixed to hollow shaft (372) and rotating drive gear (374), rotation of bevel gear (375) also rotates hollow shaft (372) and rotating drive gear (374) in the same direction. Therefore, rotation of finger wheel (325) about axis (L1) causes rotation of rotating drive gear (374) about axis (L2).

Figure 15A:
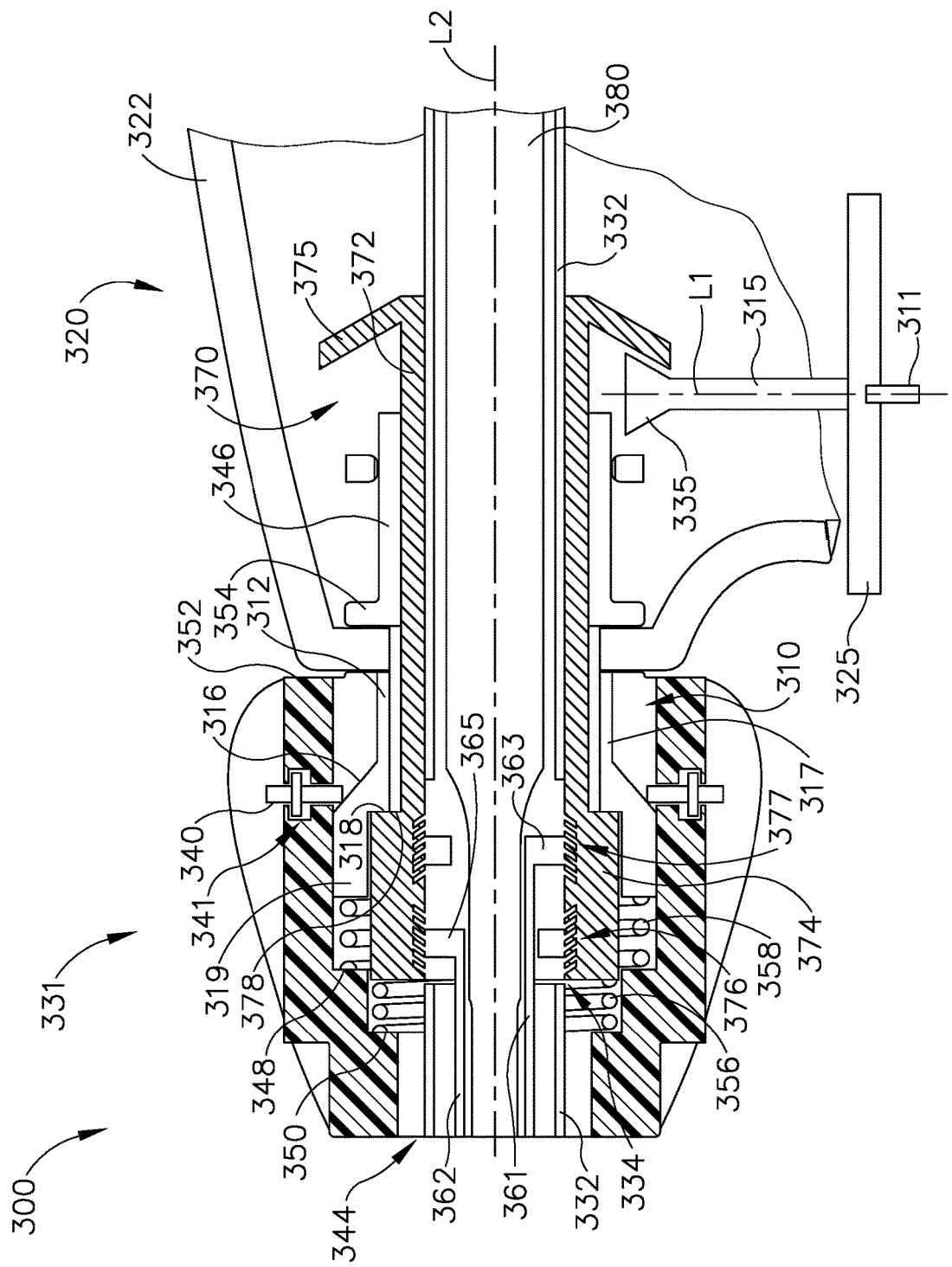
FIG. 15A depicts a side cross-sectional view of the shaft assembly and handle assembly of FIG. 12, where the articulation and rotations features are in a locked position.
Figure 15B:
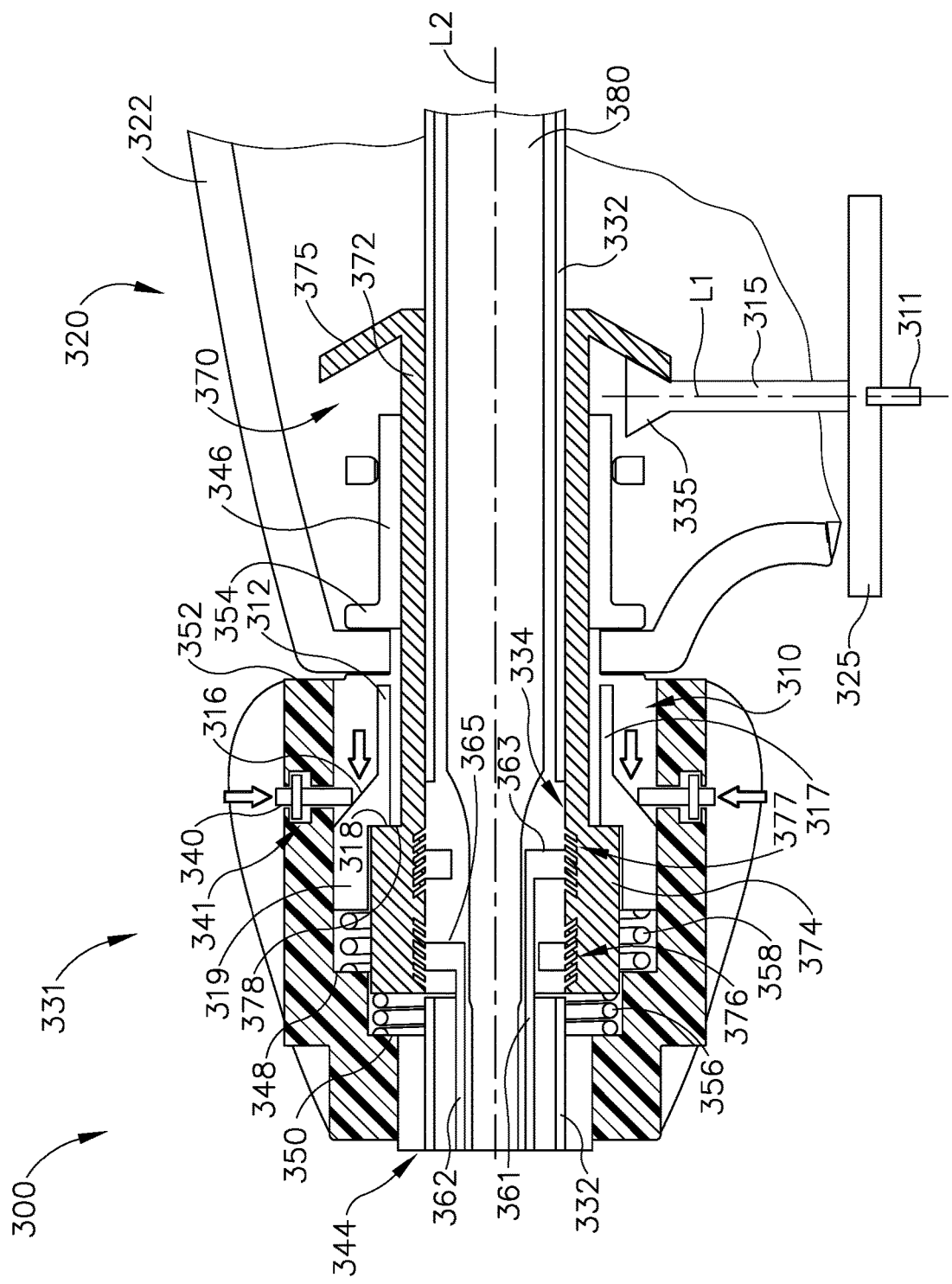
FIG. 15B depicts a side cross-sectional view of the shaft assembly and handle assembly of FIG. 12, where the articulation and rotation features are in an unlocked position.
Figure 15C:
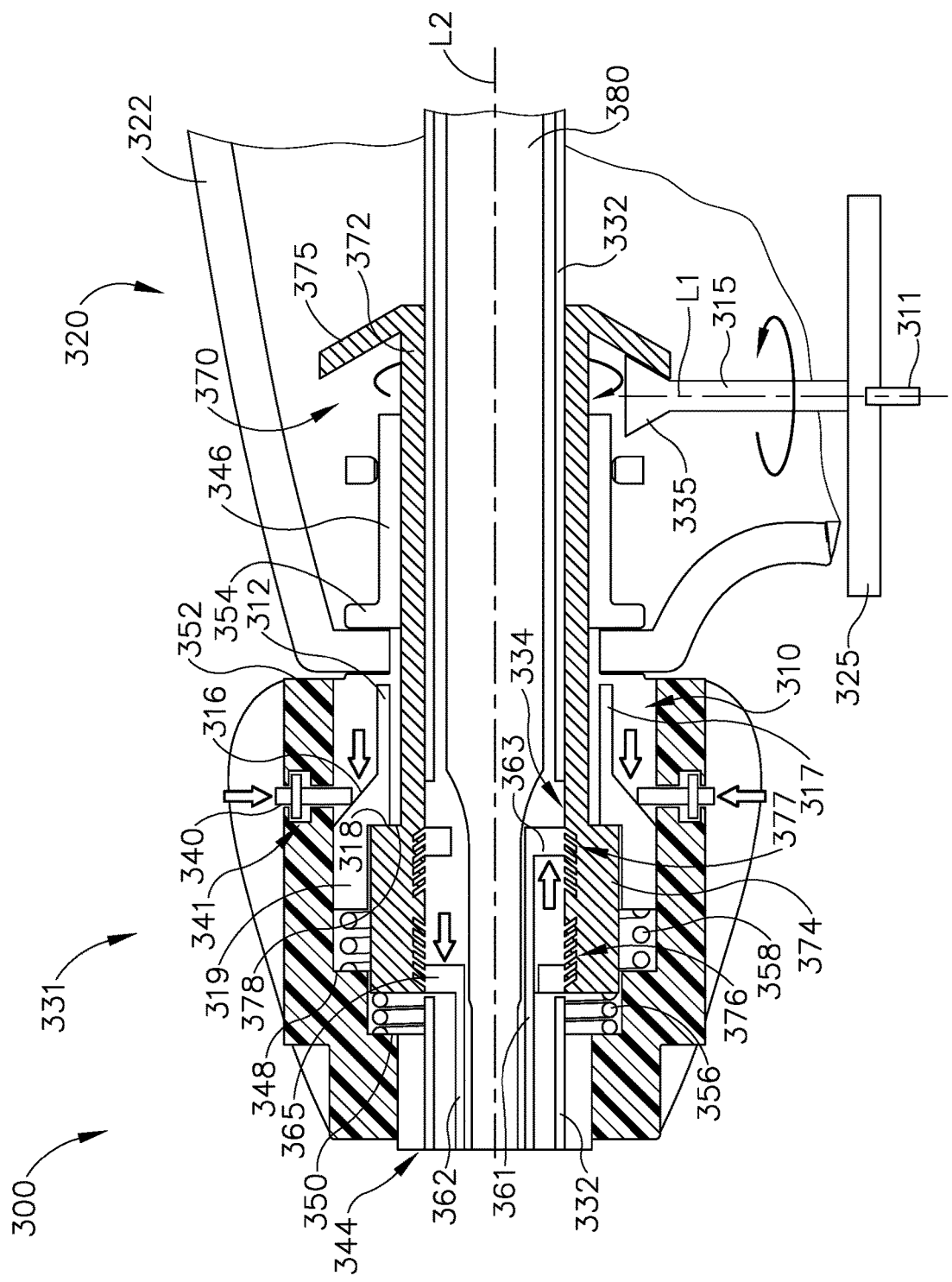
FIG. 15C depicts a side cross-sectional view of the shaft assembly and handle assembly of FIG. 12, where the articulation and rotation features are in the unlocked position and the end effector is in the first articulated position shown in FIG. 6B.
Figure 15D:
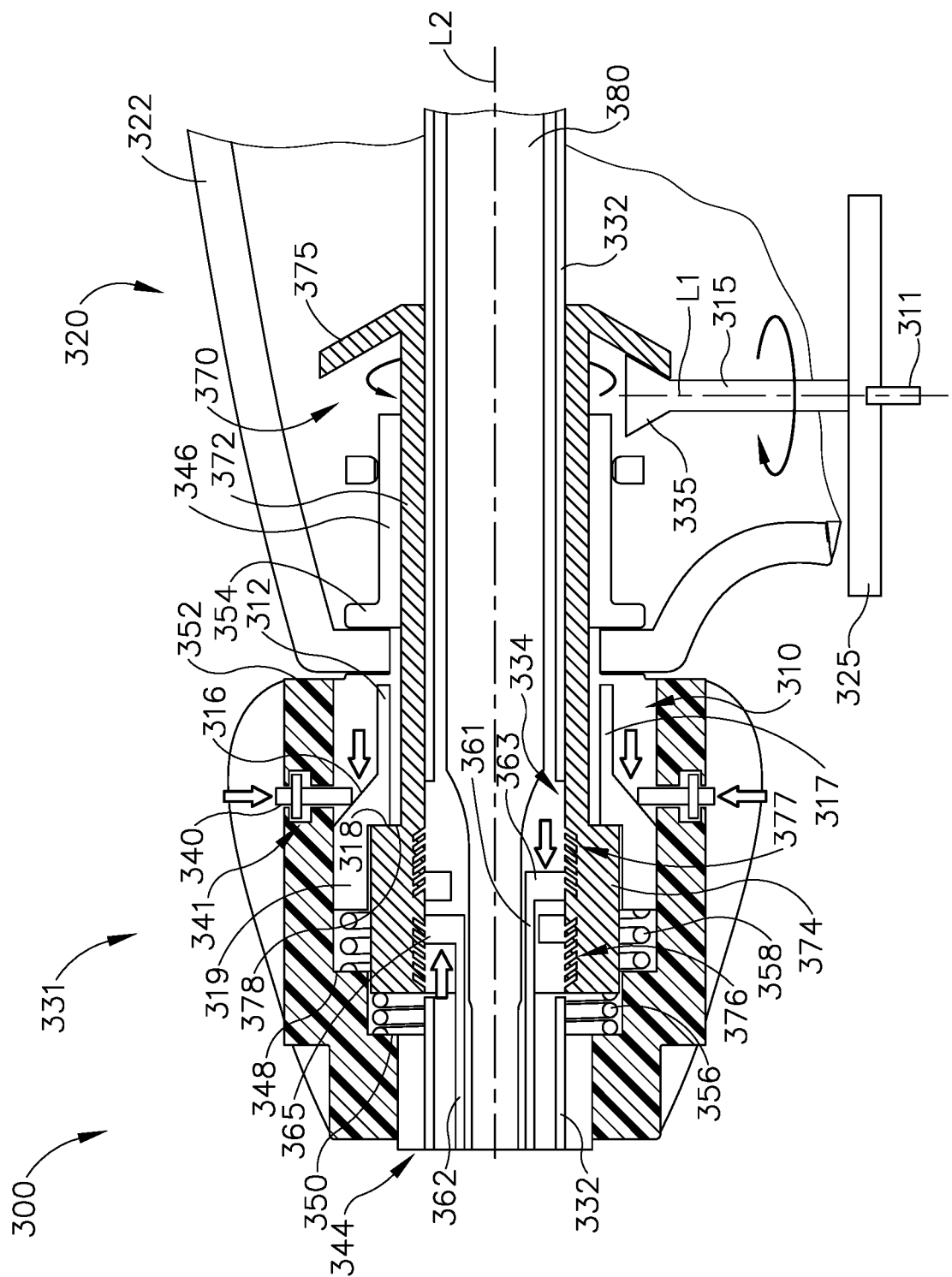
FIG. 15D depicts a side cross-sectional view of the shaft assembly and handle assembly of FIG. 12, where the articulation and rotation features are in the unlocked position and the end effector is in the second articulated position shown in FIG. 6C.

As seen in FIGS. 15A-15D, rotating drive gear (374) includes a pair of opposed-pitch threading (376, 377) and an external annular step surface (378). Opposed-pitch threading (376, 377) faces toward hollow portion (379). It should be understood that if threading (376) has a right-handed pitch orientation, threading (377) would have a left-handed pitch orientation or vice versa. Translating drive gear (363) meshes with threading (377) while translating drive gear (365) meshes with threading (376). It should be understood that translating drive gears (363, 365) are mechanically grounded with proximal outer shaft (332). Therefore, rotation of rotating drive gear (374) relative to proximal outer shaft (332) actuates translating members (361, 362) via meshing of translating drive gears (363, 365) and respective threading (377, 376). Due to the opposing orientation of threading (376, 377), rotation of rotating drive member (374) in a first direction will actuate translating drive gear (365) and translating member (362) in a distal direction while simultaneously translating drive gear (363) and translating member (361) in a distal direction as shown in FIG. 15C. This position may correspond with the articulated state of end effector (40) shown in FIG. 6B. Also, rotation of rotating drive member (374) in a second direction will actuate translating driver gear (365) and translating member (362) in a proximal direction while simultaneously translating driver gear (363) and translating member (361) in a distal direction as shown in FIG. 15D. This position may correspond with the articulated state of end effector (40) shown in FIG. 6C.

Conical rotation lock (310) includes a pair of proximally presented tabs (312), an intermediate portion (317), a conical portion (316), and a distal end (319) having an internal step (318). As shown in FIG. 15A, spring (348) is located between first annular wall (348) and distal end (319) to impart a biasing force on conical lock (310) so that proximally presented tabs (312) extend though locking slots (342). A portion of body (322) is located between proximal exterior surface (352) and radial protrusion (354) of knob (331). Proximally presented tabs (312) extend through locking slots (342) to make contact with the portion of body (322) located between proximal exterior surface (352) and radial protrusion (342). The contact between proximally presented tabs (312) and body (322) provides a frictional braking force preventing rotation on conical lock (310). The frictional braking force travels through spring (358) to first annular wall (348) of knob (331). Alternatively, some other kind of feature(s) may be provided to couple knob (331) with conical lock (310). In either case, the frictional braking force between distally presented tabs (312) and body (322) prevents rotation of knob (331) about longitudinal axis (L2). Knob (331) and shaft assembly (330) are thus effectively locked in rotational position when conical lock (310) is in the proximal position shown in FIG. 15A. In some versions, body (322) includes an annular array of recesses that are configured to receive proximally presented tabs (312), thereby providing an enhanced braking effect when conical rotation lock is in the proximal position shown in FIG. 15A.

Additionally, as shown in FIG. 15A, spring (356) is located between second annular wall (350) and a distal end of rotating drive gear (374) to impart a biasing force on rotating drive gear (374) so that annular step surface (378) contacts internal step (318) of conical lock (310). The proximal bias of rotating drive gear (374) creates a frictional braking force between the complementary threading (376, 377) of rotating drive gear (374) and the threading of translating drive gears (365, 363), respectively. This frictional braking force is sufficient to inhibit rotation of articulation drive shaft (370) about longitudinal axis (L2). Therefore, a user may be prevented from rotating articulation finger wheel (325) about pin (311) if bevel gears (335, 375) are meshed. In other words, the frictional braking force provided by the proximal bias of rotating driver gear (374) acts as an articulation lock for articulation control assembly (300) when knob (331) is in the position shown in FIG. 15A.

Alternatively, the proximal bias of rotating drive gear (374) may place bevel gear (375) in a proximal position such that bevel gear (375) does not mesh with bevel gear (335). Thus, rotation of articulation finger wheel (325) about axis (L1) would not rotate articulation drive shaft (370) about axis (L2), such that articulation control assembly (300) would effectively be inoperable when knob (331) is in the position shown in FIG. 15A.

As previously mentioned, unlocking pins (340) are slidably housed within pin slots (341). Conical portion (316) of conical lock (310) is located directly under the bottom of unlocking pins (340). As shown between FIG. 15A and FIG. 15B, unlocking pins (340) may be pressed inwardly to make contact with conical portion (316) of conical lock (310). The inward motion of unlocking pins (340) imparts a camming force on conical portion (316) of conical lock (310). The camming force imparted on conical lock (310) may overcome the biasing forces provided springs (348, 350). Therefore, conical lock (310) travels in the distal direction. When this occurs, proximally presented pins (312) of conical lock (310) no longer make contact with the portion of body (322) located between proximal exterior surface (352) and radial protrusion (354) of knob (331). In other words, conical lock (310) and body (322) no longer impart a frictional braking force on knob (331). With no frictional braking force imparted on knob (331), knob (331) and shaft assembly (330) are free to rotate about longitudinal axis (L2).

It should be understood that rotation of knob (331) in the position shown in FIG. 15B also rotates translating members (361, 362) and translating drive gears (363, 365). However, contact between internal step (318) of conical lock (310) and annular step surface (378) of rotating drive gear (374) imparts a frictional force such that articulation drive shaft (370) unitarily rotates with conical lock (310) and knob (331). Therefore, there is no effective rotation between translating drive gears (363, 365) and rotating drive gear (374). Thus, rotation of knob (331) and shaft assembly (330) in the position shown in FIG. 15B do not cause any unintentional articulation of end effector (40). However, it should be understood that if a user holds articulation finger wheel (325) while rotation knob (331) and shaft assembly (330) are in the position shown in FIG. 15B, the friction force between internal step (318) of conical lock (310) and annular step surface (378) will be overcome, leading to rotation between translating drive gears (363, 365) and rotation drive gear (374), and therefore articulation of end effector (40).

Additionally, when unlocking pins (340) force conical lock (310) in the distal direction as shown in FIG. 15B, internal step (318) of conical lock (310) contacts annular step surface (378) of rotating drive gear (374) to force articulation drive shaft (370) in the distal direction. Thus, complementary threading (376, 377) of rotating drive gear (374) and the threading of translating drive gears (365, 363), respectively, are aligned. This alignment eliminates the frictional braking force between complementary threading (376, 377) of rotating drive gear (374) and threading of translating drive gears (365, 363), respectively. A user may then rotate articulation finger wheel (325) about axis (L1) to rotate articulation drive shaft (370) about longitudinal axis (L2). A user may therefore no longer be prevented from rotating articulation finger wheel (325) about pin (311) when bevel gears (335, 375) are meshed. In other words, articulation control assembly (300) is in an unlocked configuration when conical lock (310) is in the position shown in FIG. 15B.

Alternatively, the distal movement of rotating drive gear (374) may place bevel gear (375) in a distal position such that bevel gear (375) and bevel gear (35) mesh. Then, rotation of articulation finger wheel (325) about axis (L1) would rotate articulation drive shaft (370) about axis (L2), therefore effectively unlocking articulation control assembly (300) when knob (331) is in the position shown in FIG. 15B.

As shown in FIG. 15C, a user may rotate articulation finger wheel (325) in a first direction about axis (L1) while holding knob (331), leading to rotation of drive shaft (315) and bevel gear (335) about axis (L1). Due to bevel gear (335) meshing with bevel gear (375), bevel gear (375) and the rest of articulation drive shaft (370) rotate about longitudinal axis (L2) in a first direction. Because a user is preventing rotation of knob (331), rotation of drive shaft (370) leads to rotation of rotating drive gear (374) in the first direction relative to proximal outer shaft (332). Due to the opposed-pitch threading (376, 377) meshing with translating drive gears (365, 363) respectively, translating drive gear (365) and translating member (362) actuate in a distal direction while translating driver gear (363) and translating member (361) simultaneously actuate in a proximal direction. This position may correspond with the articulated state of end effector (40) shown in FIG. 6B.

Alternatively, as shown in FIG. 15D, a user may rotate articulation finger wheel (325) in a second direction about axis (L1) while holding knob (331), leading to drive shaft (315) and bevel gear (335) rotating about axis (L1). Due to bevel gear (335) meshing with bevel gear (375), bevel gear (375) and the rest of articulation drive shaft (370) rotate about longitudinal axis (L2) in a second direction. Because a user is preventing rotation of knob (331), rotation of drive shaft (370) leads to rotation of rotating drive gear (374) in the second direction relative to proximal outer shaft (332). Due to the opposed-pitch threading (376, 377) meshing with translating drive gears (365, 363) respectively, translating drive gear (365) and translating member (362) actuate in a proximal direction while translating driver gear (363) and translating member (361) simultaneously actuate in a distal direction. This position may correspond with the articulated state of end effector (40) shown in FIG. 6C.

When a user releases unlocking pins (340), springs (348, 350) resiliently return articulation drive shaft (370) and conical lock (310) back into the position shown in FIG. 15A, thereby preventing rotation of knob (331) and shaft assembly (330) about longitudinal axis (L2), and also preventing articulation of end effector (40) through rotation of articulation control assembly (300).

Therefore, a user may selectively unlock the rotation features of knob (331) and shaft assembly (330) while unlocking the articulation features of articulation control assembly (300) by pushing unlocking pins (340) inwardly. A user may then rotate knob (331) and shaft assembly (330) to a desired rotation position relative to longitudinal axis (L2) and simultaneously articulate end effector (40) to a desired articulated position. Once user releases unlocking pins (340), knob (331), shaft assembly (330), and end effector (40) will remain in the desired positions until unlocking pins (340) are pushed inwardly again.

In the foregoing example, conical lock (310) is configured to transition between a first state (proximal position) and a second state (distal position). In the first state, conical lock (310) is configured to simultaneously lock rotation of shaft assembly (330) about the longitudinal axis (L2) and articulation of end effector (40). In the second state, conical lock (310) is configured to simultaneously unlock rotation of shaft assembly (330) about the longitudinal axis (L2) and articulation of end effector (40). In some other versions, separate components or features are used to lock/unlock rotation of shaft assembly (330) about the longitudinal axis (L2) and articulation of end effector (40). For instance, a first locking feature may selectively lock/unlock rotation of shaft assembly (330) about the longitudinal axis (L2); while a second locking feature may selectively lock/unlock articulation of end effector (40). In such versions, a single control feature (e.g., button, slider, lever, etc.) may be used to simultaneously actuate the first and second locking features. Alternatively, the first and second locking features may be actuated independently (e.g., by respective first and second control features). Various suitable ways in which these alternative versions may be provided will be apparent to those of ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for operating on tissue, the apparatus comprising: (a) a body assembly; (b) a shaft assembly extending distally from the body assembly, wherein the shaft assembly defines a longitudinal axis; (c) an acoustic waveguide, wherein the waveguide comprises a flexible portion; (d) an articulation section coupled with the shaft assembly, wherein a portion of the articulation section encompasses the flexible portion of the waveguide, wherein the articulation section further comprises: (i) a first member, and (ii) a second member, wherein the second member is longitudinally translatable relative to the first member; (e) an articulation control assembly configured to move relative to the shaft assembly in order to longitudinally translate the second member relative to the first member; (f) an end effector comprising an ultrasonic blade in acoustic communication with the waveguide; and (g) an articulation lock, wherein the articulation lock is configured to prevent movement of the articulation control assembly relative to the shaft assembly.

Example 2

The apparatus of Example 1, wherein the shaft assembly comprises an outer sheath configured to translate from a first position to a second position, wherein articulation lock comprises: (i) a plurality of teeth located on the articulation control assembly, and (ii) a pin fixed to an outer sheath of the shaft assembly, wherein the pin is configured to mesh with the plurality of teeth when the outer sheath is in the second position.

Example 3

The apparatus of Example 2, wherein the body assembly further comprises a trigger, wherein the trigger is configured to pivot toward or away from the body assembly from a first pivotal position to a second pivotal position.

Example 4

The apparatus of Example 3, wherein the trigger is configured to translate the outer sheath from the first position to the second position in response to the trigger pivoting from the first pivotal position to the second pivotal position.

Example 5

The apparatus of Example 4, wherein the apparatus further comprises a knob rotatably connected to the body assembly, wherein the knob is configured to rotate the shaft assembly about the longitudinal axis.

Example 6

The apparatus of any one or more of Examples 4 through 5, wherein the outer sheath further comprises a splined proximal portion extending into the body assembly.

Example 7

The apparatus of Example 6, wherein the trigger further comprises a lever with a pin, wherein the pin is configured to mesh with the splined proximal portion when the trigger is in the second pivotal position.

Example 8

The apparatus of any one or more of Examples 1 through 7, wherein the articulation control assembly further comprises a rotating drive gear comprising a left-handed threading and a right-handed threading.

Example 9

The apparatus of Example 8, wherein the first member further comprises a first translating drive gear coupled to the left-handed threading of the rotating drive gear, wherein the second member further comprises a second translating drive gear coupled to the right handed threading of the rotating drive gear.

Example 10

The apparatus of Example 9, wherein the articulation lock further comprises a first biasing element in contact with the articulation control assembly, wherein the first biasing element is configured to bias articulation control assembly to a first position to prevent movement of the articulation control assembly relative to the shaft assembly.

Example 11

The apparatus of Example 10, wherein the first biasing element is configured to impart a frictional braking force between the left-handed threading of the rotating drive gear and the first translating drive gear of the first member to prevent movement of the articulation control assembly relative to the shaft assembly.

Example 12

The apparatus of any one or more of Examples 10 through 11, wherein the articulation lock further comprises a conical locking member, wherein the conical locking member is configured to actuate from a third position to a fourth position such that articulation control assembly actuates from the first position to a second position, wherein the articulation control assembly in configured to move relative to the shaft assembly in the second position.

Example 13

The apparatus of Example 12, wherein the conical locking member is in contact with a second biasing element, wherein the second biasing element is configured to bias the conical locking member to the third position.

Example 14

The apparatus of Example 13, wherein the apparatus further comprises knob rotatably connected to the body assembly, wherein the knob is configured to rotate the shaft assembly about the longitudinal axis, wherein the knob houses the conical locking member.

Example 15

The apparatus of Example 14, wherein the conical locking member is configured to prevent the knob from rotating the shaft assembly about the longitudinal axis in the third position.

Example 16

The apparatus of Example 15, wherein the knob comprises an unlocking pin, wherein the unlocking pin is configured to actuate the conical locking member from the third position to the fourth position.

Example 17

The apparatus of any one or more of Examples 15 through 16, wherein conical locking member is further configured to lock the articulation control assembly in the third position.

Example 18

An apparatus for operating on tissue, the apparatus comprising: (a) a body assembly; (b) a shaft extending distally from the body assembly, wherein the shaft defines a longitudinal axis; (c) an articulation section coupled with the shaft; (d) an end effector coupled with the articulation section, wherein the end effector comprises a working element configured to engage tissue; (e) an articulation drive assembly operable to drive articulation of the articulation section to thereby deflect the end effector from the longitudinal axis, wherein the articulation drive assembly comprises: (i) a first translating driver, and (ii) a second translating driver; and (f) an articulation lock assembly configured to engage the articulation drive assembly to fix the first translating driver relative to the second translating driver.

Example 19

The apparatus of Example 18, wherein the articulation lock is biased fix the first translating driver relative to the second translating driver.

Example 20

An apparatus for operating on tissue, the apparatus comprising: (a) a body assembly; (b) a shaft extending distally from the body assembly, wherein the shaft defines a longitudinal axis; (c) an articulation section coupled with the shaft; (d) an end effector coupled with the articulation section; (e) a knob rotatably coupled to the body assembly, wherein the knob is configured to rotate the shaft, the articulation section, and the end effector about the longitudinal axis; (e) a first pair of translating members, wherein the first pair of translating members is operable to actuate the articulation section to thereby deflect the end effector from the longitudinal axis; (f) a drive assembly in communication with the first pair of translating members, wherein the drive assembly is configured to translate the first pair of translating members to actuate the articulation section; and (g) a lock assembly, wherein the lock assembly is configured to simultaneously prevent rotation a knob about the longitudinal axis and translation of the first pair of translating members.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising: (a) a shaft assembly, wherein the shaft assembly defines a longitudinal axis; (b) an acoustic waveguide, wherein the waveguide comprises a flexible portion; (c) an articulation section coupled with the shaft assembly, wherein a portion of the articulation section encompasses the flexible portion of the waveguide, wherein the articulation section further comprises: (i) a first member, and (ii) a second member, wherein the second member is longitudinally translatable relative to the first member; (d) an articulation control assembly configured to move relative to the shaft assembly in order to longitudinally translate the second member relative to the first member; (e) an end effector comprising an ultrasonic blade in acoustic communication with the waveguide, wherein the articulation control assembly is configured to deflect the end effector from the longitudinal axis in a plurality of articulated positions; and (f) an articulation lock configured to actuate into a locked position, wherein the articulation lock is configured to simultaneously prevent rotation of the shaft assembly and movement of the articulation control assembly relative to the shaft assembly in the locked position when the end effector is in a straight position and a first articulated position of the plurality of articulated positions.

2. The apparatus of claim 1, wherein the shaft assembly comprises an outer sheath configured to translate from a first position to a second position, wherein the articulation lock comprises:
(i) a plurality of teeth located on the articulation control assembly, and
(ii) a pin fixed to the outer sheath of the shaft assembly, wherein the pin is configured to mesh with the plurality of teeth when the outer sheath is in the second position.

3. The apparatus of claim 2, further comprising a body assembly, wherein the body assembly further comprises a trigger, wherein the trigger is configured to pivot toward or away from the body assembly from a first pivotal position to a second pivotal position.

4. The apparatus of claim 3, wherein the trigger is configured to translate the outer sheath from the first position to the second position in response to the trigger pivoting from the first pivotal position to the second pivotal position.

5. The apparatus of claim 4, wherein the apparatus further comprises a knob rotatably connected to the body assembly, wherein the knob is configured to rotate the shaft assembly about the longitudinal axis.

6. The apparatus of claim 4, wherein the outer sheath further comprises a splined proximal portion extending into the body assembly.

7. The apparatus of claim 6, wherein the trigger further comprises a lever with a lock pin, wherein the lock pin is configured to mesh with the splined proximal portion when the trigger is in the second pivotal position.

8. The apparatus of claim 1, wherein the articulation control assembly further comprises a rotating drive gear comprising a left-handed threading and a right-handed threading.

9. The apparatus of claim 8, wherein the first member further comprises a first translating drive gear coupled to the left-handed threading of the rotating drive gear, wherein the second member further comprises a second translating drive gear coupled to the right handed threading of the rotating drive gear.

10. The apparatus of claim 9, wherein the articulation lock further comprises a first biasing element in contact with the articulation control assembly, wherein the first biasing element is configured to bias the articulation control assembly to a first position to prevent movement of the articulation control assembly relative to the shaft assembly.

11. The apparatus of claim 10, wherein the first biasing element is configured to impart a frictional braking force between the left-handed threading of the rotating drive gear and the first translating drive gear of the first member to prevent movement of the articulation control assembly relative to the shaft assembly.

12. The apparatus of claim 10, wherein the articulation lock further comprises a conical locking member, wherein the conical locking member is configured to actuate from a third position to a fourth position such that the articulation control assembly actuates from the first position to a second position, wherein the articulation control assembly in configured to move relative to the shaft assembly in the second position.

13. The apparatus of claim 12, wherein the conical locking member is in contact with a second biasing element, wherein the second biasing element is configured to bias the conical locking member to the third position.

14. The apparatus of claim 13, further comprising a body assembly, wherein the apparatus further comprises knob rotatably connected to the body assembly, wherein the knob is configured to rotate the shaft assembly about the longitudinal axis, wherein the knob houses the conical locking member.

15. The apparatus of claim 14, wherein the conical locking member is configured to prevent the knob from rotating the shaft assembly about the longitudinal axis in the third position.

16. The apparatus of claim 15, wherein the knob comprises an unlocking pin, wherein the unlocking pin is configured to actuate the conical locking member from the third position to the fourth position.

17. The apparatus of claim 15, wherein conical locking member is further configured to lock the articulation control assembly in the third position.

18. An apparatus for operating on tissue, the apparatus comprising:
(a) a shaft, wherein the shaft defines a longitudinal axis;
(b) an articulation section coupled with the shaft;
(c) an end effector coupled with the articulation section, wherein the end effector comprises a working element configured to engage tissue;
(d) an articulation drive assembly operable to drive articulation of the articulation section to thereby deflect the end effector from the longitudinal axis from an aligned position to an articulated position, wherein the articulation drive assembly comprises:
(i) a first translating driver,
(ii) a second translating driver, and
(iii) a rotational driver configured to rotate about an axis in order to actuate the first translating driver relative to the second translating driver in order to deflect the end effector from the longitudinal axis; and
(e) an articulation lock assembly configured to actuate into a locked position to engage and thereby prevent rotation of the rotational driver of the articulation drive assembly about the axis to fix the first translating driver relative to the second translating driver when the end effector is in both the aligned position and the articulated position.

19. The apparatus of claim 18, wherein the articulation lock assembly is biased to fix the first translating driver relative to the second translating driver.

20. An apparatus for operating on tissue, the apparatus comprising: (a) a shaft, wherein the shaft defines a longitudinal axis; (b) an articulation section coupled with the shaft; (c) an end effector coupled with the articulation section; (d) a knob, wherein the knob is configured to rotate the shaft, the articulation section, and the end effector about the longitudinal axis; (e) a first pair of translating members, wherein the first pair of translating members is operable to actuate the articulation section to thereby deflect the end effector from the longitudinal axis from an aligned position to an articulated position; (f) a drive assembly in communication with the first pair of translating members, wherein the drive assembly is configured to translate the first pair of translating members to actuate the articulation section; and (g) a lock assembly, wherein the lock assembly is configured to simultaneously prevent rotation of the knob about the longitudinal axis and translation of the first pair of translating members when the end effector is in both the aligned position and the articulated position.

* * * * *